US006251284B1

(12) United States Patent
Bischof et al.

(10) Patent No.: US 6,251,284 B1
(45) Date of Patent: Jun. 26, 2001

(54) SYSTEMS AND METHODS WHICH OBTAIN A UNIFORM TARGETED VOLUME OF CONCENTRATED RED BLOOD CELLS IN DIVERSE DONOR POPULATIONS

(75) Inventors: Daniel F Bischof, McHenry; Matthew E Likens, Libertyville, both of IL (US); Richard P Goldhaber, Wayzata, MN (US); Jose C Deniega, Lake Forest; Daniel H Duff, Irvine, both of CA (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 08/979,160

(22) Filed: Nov. 26, 1997

Related U.S. Application Data

(63) Continuation-in-part of application No. 08/512,807, filed on Aug. 9, 1995, now Pat. No. 5,762,791.

(51) Int. Cl.⁷ .......................... B01D 21/26; B01D 21/30; A61M 1/38
(52) U.S. Cl. .............................. 210/739; 210/85; 210/97; 210/109; 210/143; 210/782; 210/787; 210/789; 494/37; 494/43; 494/45; 604/4.01; 604/6.01; 604/6.02; 604/6.03; 604/6.04; 604/65; 604/67
(58) Field of Search .................................. 210/85, 86, 90, 210/97, 109, 134, 143, 321.67, 321.68, 321.78, 739, 782, 787, 789; 604/4, 5, 6, 65, 67, 4.01, 5.01, 6.01, 6.02, 6.04, 6.05, 6.03; 494/37, 43, 45

(56) References Cited

U.S. PATENT DOCUMENTS 3,916,892   11/1975   Latham, Jr. .

| 4,185,629 | 1/1980 | Cullis et al. . |
| 4,447,191 | 5/1984 | Bilstad et al. .............................. 604/6 |
| 4,458,539 | 7/1984 | Bilstad et al. .............................. 604/6 |
| 4,464,167 | 8/1984 | Schoendorfer et al. .................. 604/6 |
| 4,481,827 | 11/1984 | Bilstad et al. .............................. 604/6 |
| 4,498,983 | 2/1985 | Bilstad et al. ........................... 210/97 |
| 4,501,531 | 2/1985 | Bilstad et al. ........................... 604/67 |
| 4,605,503 | 8/1986 | Bilstad et al. ................... 210/321.65 |
| 4,648,866 | 3/1987 | Malbrancq et al. ....................... 604/5 |
| 4,655,742 | 4/1987 | Vantard .................................... 604/6 |
| 4,657,529 | 4/1987 | Prince et al. .............................. 604/6 |
| 4,675,117 | 6/1987 | Neumann et al. ..................... 210/789 |
| 4,708,714 | 11/1987 | Larsson et al. ........................... 604/5 |
| 4,713,176 | 12/1987 | Schoendorfer et al. ............. 210/645 |

(List continued on next page.)

FOREIGN PATENT DOCUMENTS

WO 97/05938   *   2/1997   (WO) .

*Primary Examiner*—John Kim
(74) *Attorney, Agent, or Firm*—Daniel D. Ryan; Bradford R. L. Price; Denise Serewicz

(57) ABSTRACT

Blood separation systems and methods draw whole blood from a blood donor selected from a population of blood donors. The whole blood of the selected blood donor has a known hematocrit value that varies within the population of blood donors according to morphology of the selected blood donor. The systems and methods operate a pump in the inlet line to convey a volume of whole blood from the donor at a commanded flow rate for processing into plasma constituent and concentrated red blood cells. The systems and methods set the commanded flow rate to vary the volume of whole blood conveyed over time as a function of the known hematocrit value of the selected donor. The systems and methods obtain, after processing the whole blood volume, a targeted volume of concentrated red blood cells, which is substantially constant for the population of blood donors despite variances in known hematocrit values among the donors.

9 Claims, 15 Drawing Sheets

U.S. PATENT DOCUMENTS

| | | |
|---|---|---|
| 4,755,300 | 7/1988 | Fischel et al. .................. 210/321.68 |
| 4,769,001 | 9/1988 | Prince ....................................... 604/4 |
| 4,850,995 | 7/1989 | Tie et al. .................................. 604/6 |
| 4,851,126 | 7/1989 | Schoendorfer ....................... 210/651 |
| 4,879,040 | 11/1989 | Prince et al. .......................... 210/651 |
| 4,883,462 | 11/1989 | Williamson et al. .................. 604/66 |
| 4,915,848 | 4/1990 | Carmen et al. ....................... 210/782 |
| 4,935,002 | 6/1990 | Gordon .................................... 604/4 |
| 4,944,883 | 7/1990 | Schoendorfer et al. ............. 210/782 |
| 4,968,295 | 11/1990 | Neumann ................................ 604/6 |
| 4,985,153 * | 1/1991 | Kuroda et al. ....................... 210/782 |
| 4,994,188 | 2/1991 | Prince ................................... 210/636 |
| 4,995,268 | 2/1991 | Ash et al. ............................... 604/65 |
| 5,034,135 | 7/1991 | Fischel ................................. 210/651 |
| 5,053,121 | 10/1991 | Schoendorfer et al. ............... 210/90 |
| 5,069,792 | 12/1991 | Prince et al. .......................... 210/651 |
| 5,112,298 | 5/1992 | Prince et al. ............................. 604/6 |
| 5,135,667 | 8/1992 | Schoendorfer ....................... 210/782 |
| 5,171,456 | 12/1992 | Hwang et al. ........................ 210/782 |
| 5,178,603 | 1/1993 | Prince ....................................... 604/6 |
| 5,188,588 | 2/1993 | Schoendorfer et al. ................. 604/4 |
| 5,194,145 | 3/1993 | Schoendorfer ......................... 210/90 |
| 5,211,849 | 5/1993 | Kitaevich et al. .................... 210/645 |
| 5,234,608 | 8/1993 | Duff ..................................... 210/651 |
| 5,298,171 | 3/1994 | Biesel .................................. 210/739 |
| 5,318,512 | 6/1994 | Neumann ................................ 604/6 |
| 5,370,802 | 12/1994 | Brown .................................. 210/782 |
| 5,376,263 | 12/1994 | Fischel ................................. 210/651 |
| 5,387,187 | 2/1995 | Fell et al. ................................. 604/6 |
| 5,421,812 | 6/1995 | Langley et al. .......................... 604/4 |
| 5,423,738 | 6/1995 | Robinson et al. ....................... 604/4 |
| 5,427,695 | 6/1995 | Brown et al. ........................ 210/782 |
| 5,437,598 | 8/1995 | Antwiler ................................. 604/6 |
| 5,437,624 | 8/1995 | Langley .................................. 604/4 |
| 5,443,451 | 8/1995 | Chapman et al. .................... 604/153 |
| 5,460,493 | 10/1995 | Deniega et al. ................. 417/477.2 |
| 5,494,592 | 2/1996 | Latham, Jr. et al. ................. 210/782 |
| 5,496,265 | 3/1996 | Langley et al. .......................... 604/5 |
| 5,505,685 | 4/1996 | Antwiler ................................ 494/37 |
| 5,605,842 | 2/1997 | Langley et al. ...................... 436/177 |
| 5,762,791 * | 6/1998 | Deniega et al. ................ 210/321.67 |

* cited by examiner

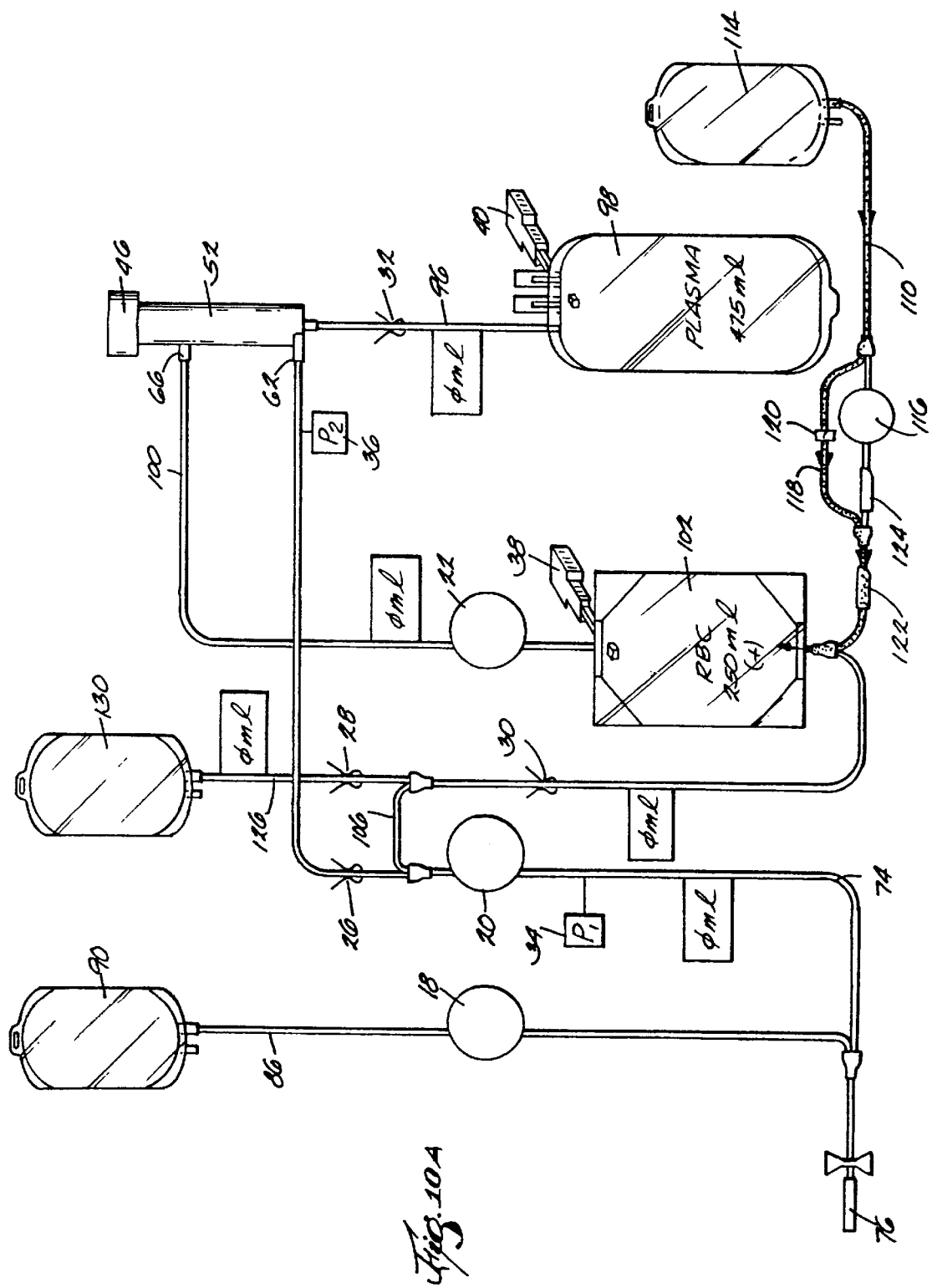

US 6,251,284 B1

SYSTEMS AND METHODS WHICH OBTAIN A UNIFORM TARGETED VOLUME OF CONCENTRATED RED BLOOD CELLS IN DIVERSE DONOR POPULATIONS

RELATED APPLICATION

This application is a continuation-in-part of application Ser. No. 08/512,807 filed Aug. 9, 1995, now U.S. Pat. No. 5,762,791.

FIELD OF THE INVENTION

The invention generally relates to blood collection and processing systems and methods. In a more particular sense, the invention relates to systems and methods for collecting concentrated red blood cells for transfusion or long term storage.

BACKGROUND OF THE INVENTION

Today, most whole blood collected from donors is not itself stored and used for transfusion. Instead, the whole blood is separated into its clinically proven components (typically red blood cells, platelets, and plasma), which are themselves individually stored and used to treat a multiplicity of specific conditions and diseased states. For example, the red blood cell component is used to treat anemia; the concentrated platelet component is used to control thrombocytopenic bleeding; and the platelet-poor plasma component is used as a volume expander or as a source of Clotting Factor VIII for the treatment of hemophilia.

Systems composed of multiple, interconnected plastic bags have met widespread use and acceptance in manually collecting these blood components for storage. A typical manual collection procedure collects 450 ml of whole blood from a donor in a primary bag. The donor departs, and the primary bag is centrifuged to separate the whole blood into plasma and red blood cells. For a typical donor, the manual collection procedure yields about 250 ml of concentrated red blood cells and about 200 ml of plasma, which are each expressed from the primary bag into individual storage bags. A majority of the platelets reside either with the plasma or with the red blood cells, depending upon the amount of centrifugal force exerted. Leukocytes typically reside primarily with the red blood cells. These leukocytes can be removed by filtration either before or after storage and prior to transfusion.

Manual collection procedures typically produce relatively high concentrations of red blood cells, which typically have hematocrits after centrifugal separation of about 70% to 80%. Hematocrit expresses the percentage volume of red blood cells to whole, or total, blood volume. In comparison, the hematocrit of whole blood for a typical healthy donor before centrifugation is about 40% to 45%, although whole blood hematocrits do vary significantly among donors from the 30 percentile range into the 50 percentile range. In the United States, federal regulations prohibit individuals with whole blood hematocrits of 38% and below from donating blood.

In the United States, federal regulations also prohibit collecting more than 250 ml of red blood cells from an individual donor during a given collection procedure. These federal regulations further require a six week interval between red blood cell collections.

Manual and automated blood collection procedures, called plasmapheresis, have been developed for collecting increased volumes of plasma from an individual donor at more frequent intervals. During plasmapheresis, red blood cells are returned to the donor, so that greater total volumes of whole blood can be processed. The result is greater total volumes of plasma collected, which typically range between 400–450 ml (for manual plasmapheresis) up to 880 ml (for automated plasmapheresis procedures).

Fischel U.S. Pat. No. 5,034,135, entitled "Blood Fractionation System and Method," discloses a membrane separation device widely used today for performing automated plasmapheresis. The device employs a rotating microporous membrane to separate whole blood into platelet poor plasma, which is retained, and concentrated red blood cells, which are returned to the donor. Prince et al. U.S. Pat. Nos. 4,879,040 and 5,069,792 describe control systems for optimizing plasma flow using the rotating membrane device, based in part upon monitoring transmembrane pressure.

While very effective in optimizing the collection of plasma, these control systems, as implemented in the Prince et al. '040 and '792 Patents, are not practically adapted for the collection of red blood cells for storage. This is because, as implemented in the Prince et al. '040 and '792 Patents, the hematocrit of the concentrated red blood cell collected is highly dependent upon the whole blood hematocrit of the donor. That is, the hematocrit of the concentrated red blood cell output for a low hematocrit donor will be lower than the hematocrit of the concentrated red blood cell output for a high hematocrit donor.

The need still exists for systems and methods that marry the collection of red blood cells in uniformly high concentrations, comparable to those of centrifugal whole blood separation procedures, with the collection of plasma in increased volume amounts comparable to those of at least manual plasmapheresis procedures. The need particularly exists for such systems and methods that can achieve these objectives uniformly for all donors, including those having relatively low whole blood hematocrits. The need is further intensified for systems that can accomplish low cost, efficient red blood cell collection on a par with manual systems, but in an automated fashion.

SUMMARY OF THE INVENTION

The invention provides blood separation systems and methods which obtain a targeted volume of concentrated red blood cells, which is substantially constant for a diverse population of healthy blood donors, despite variances in known hematocrit values among the donors.

The systems and methods draw whole blood from a blood donor through an inlet line. The blood donor is selected from the population of blood donors. The whole blood of the selected blood donor has a known hematocrit value, which varies within the population of blood donors according to morphology of the selected blood donor. The systems and methods operate a pump in the inlet line to convey a volume of whole blood from the donor at a commanded flow rate for processing into plasma constituent and concentrated red blood cells. The systems and methods set the commanded flow rate to vary the volume of whole blood conveyed over time, at least in part, as a function of the known hematocrit value of the selected donor. In this way, the systems and methods can obtain a targeted volume of concentrated red blood cells, which is substantially constant for the population of blood donors despite variances in known hematocrit values among the donors.

In one embodiment, the systems and methods also select a targeted collection time. In this embodiment, the systems and methods set the commanded flow rate of the pump to vary the volume of whole blood conveyed over time, at least in part, as a function of both the known hematocrit value of the selected donor and the targeted collection time.

In one embodiment, the systems and methods record the known hematocrit value of the selected blood donor, a targeted collection time, and a targeted volume of concentrated red blood cells. In this embodiment, the systems and methods set the commanded flow rate of the pump to vary the volume of whole blood conveyed over time as a function of the known hematocrit value of the selected donor, the targeted collection time, and the targeted volume of concentrated red blood cells. In this way, the systems and methods can obtain the targeted volume of concentrated red blood cells for any donor in the population of blood donors, despite variances in known hematocrit values among the donors.

In one embodiment, the pump conveys the volume of whole blood into a collection container. The volume of whole blood can be centrifugally processed in the collection container to yield the plasma constituent and the targeted volume of concentrated red blood cells.

In one embodiment, the pump conveys the volume of whole blood to a multiple blood bag system. The volume of whole blood can be processed in the multiple blood bag system to yield the plasma constituent and the targeted volume of concentrated red blood cells.

In one embodiment, the pump conveys the volume of whole blood through an in line separation device to separate the volume of whole blood into plasma constituent and the targeted volume of concentrated red blood cells.

In one embodiment, the conveys the volume of whole blood through a device to separate leukocytes from the volume of whole blood.

Other features and advantages of the invention will become apparent upon review of the following description, drawings, and appended claims.

DESCRIPTION OF THE PREFERRED EMBODIMENTS

I. Extra-Corporeal On-Line Blood Processing Systems and Methods

Figure 1:
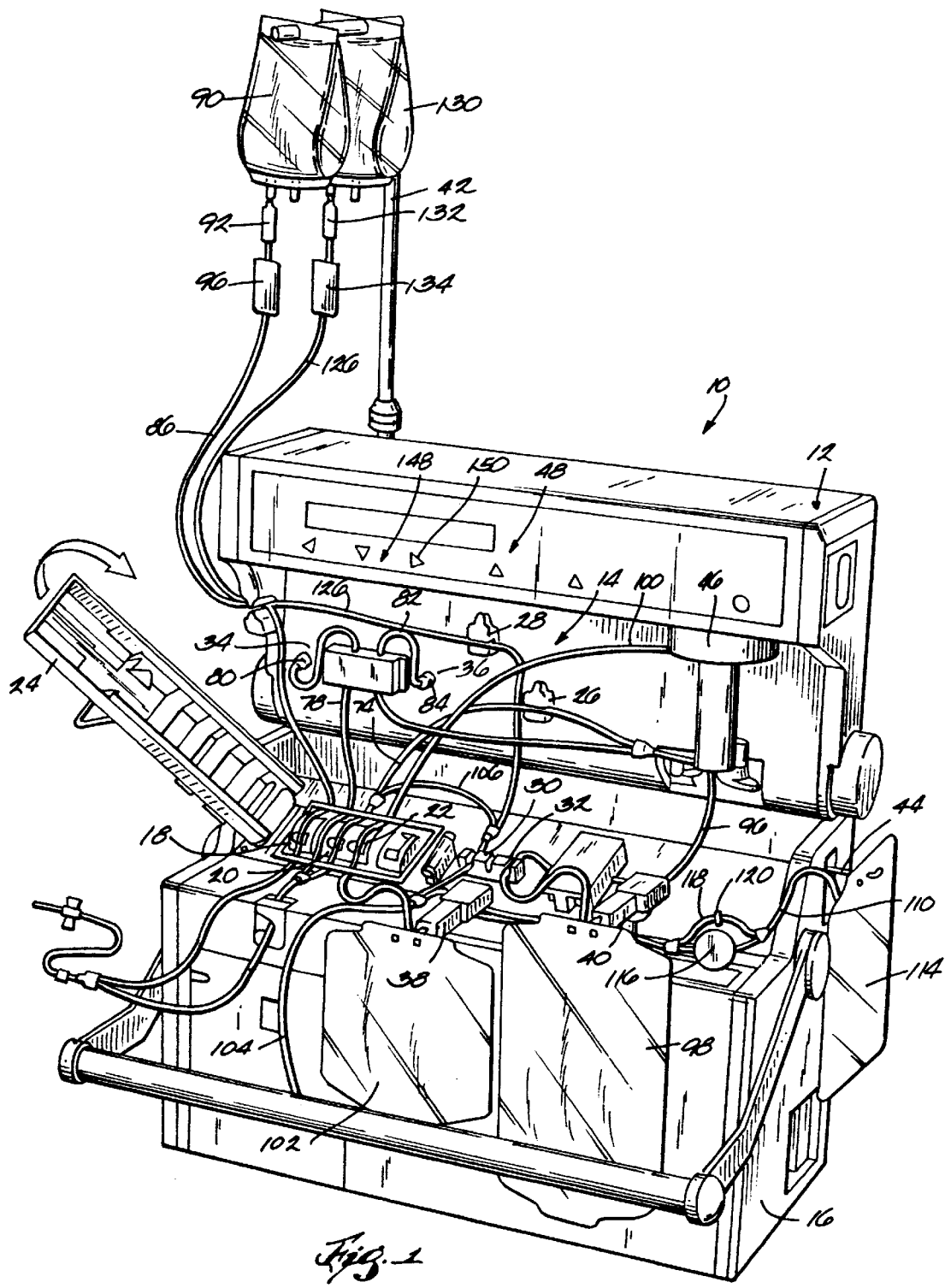
FIG. 1 is a perspective view of a blood collection system of the present invention, comprising a disposable blood processing set including a rotating microporous membrane assembly mounted on a durable blood processing device.

FIG. 1 shows a blood collection system 10 that embodies the features of the invention.

According to the invention, the system 10 serves to collect concentrated red blood cells from donors in uniformly high hematocrits comparable to those achieved by manual collection procedures, while at the same time collecting plasma in uniformly increased volume amounts comparable to those achieved by at least manual plasmapheresis procedures. The system 10 achieves these dual objectives in an automated fashion, by processing a donor's whole blood extra-corporeally over a relatively short period of time (i.e., less than 30 minutes), using a single phlebotomy needle in successive blood draw and blood return cycles. The details of these cycles will be described later.

Figure 2:
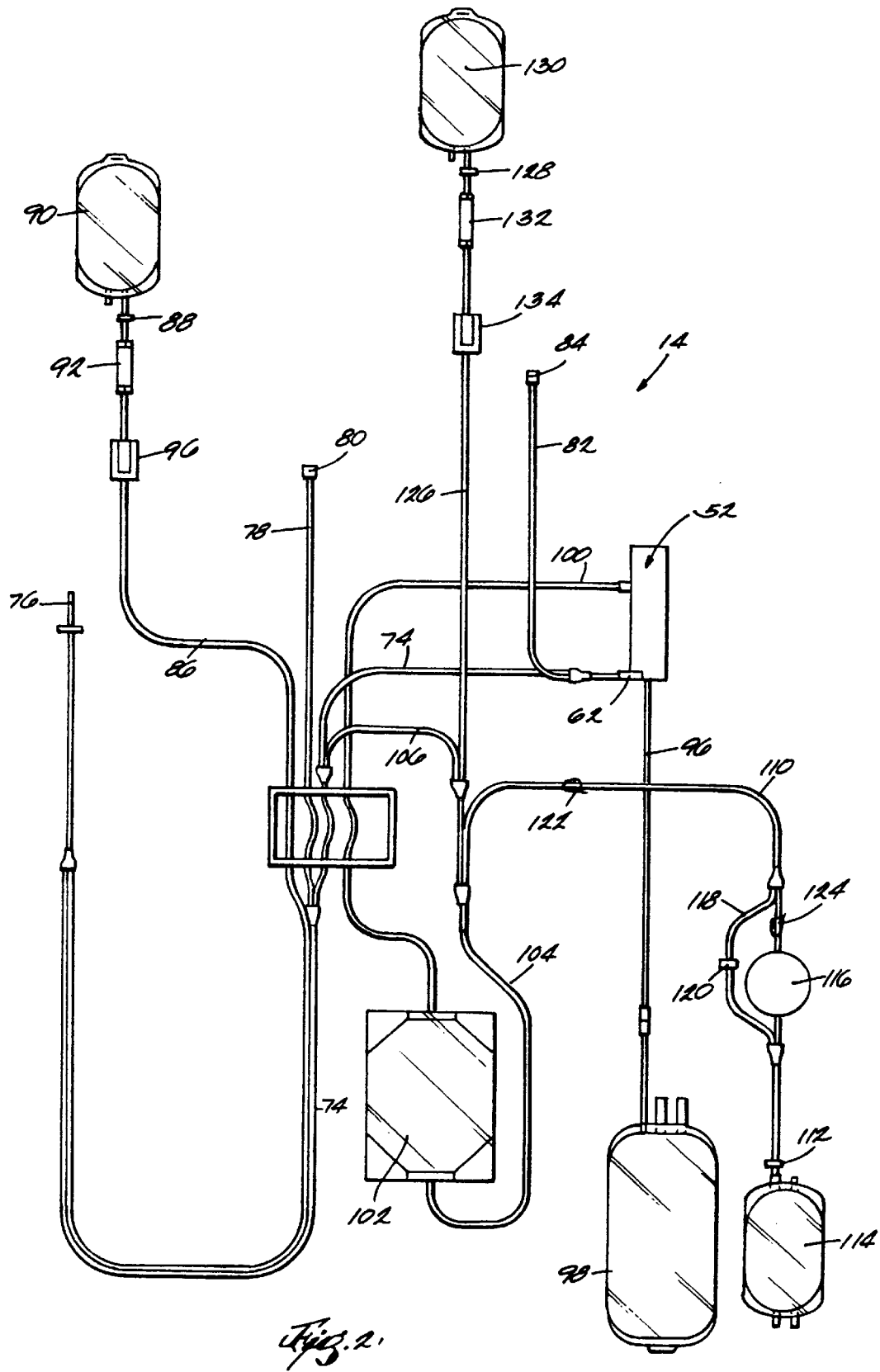
FIG. 2 is a schematic view of the disposable blood processing set associated with the blood collection system shown in FIG. 1.

As FIG. 1 shows, the system 10 includes a blood processing device 12, which constitutes a durable hardware element. The system 10 also includes a blood processing set 14 (see FIG. 2 as well), which constitutes a single use, disposable element. At the outset of a blood processing procedure, the operator mounts the set 14 (as FIG. 2 shows) in a prescribed fashion upon the device 12 (as FIG. 1 shows). At the end of the blood processing procedure, the operator removes the set 14 from the device and discards it, except for containers in which blood components are collected for storage or further processing after the donor has departed.

A. The Blood Processing Device

Referring to FIG. 1, the blood processing device 12 includes a cabinet 16 carrying various electrically operated elements. These elements include first, second, and third peristaltic pumps, respectively 18, 20, and 22. A pump cover 24, common to the pumps 18/20/22, pivots to open and close access to the pumps 18/20/22. FIG. 1 shows the pump cover 24 to be open, and the closing of the pump cover 24 is indicated by an arrow in FIG. 1. All pumps 18/20/22 are capable of operation at variable speeds under the command of an on board microprocessor-based controller 48, as will be described later. The controller 48 receives input from the operator regarding desired operating objectives and issues commands to the operative elements of the device 12 to achieve them.

The operative elements also include first, second, third, and fourth tubing clamps, respectively 26, 28, 30, and 32. In the illustrated and preferred embodiment, the clamps 26/28/30/32 are of a conventional, electrically actuated variety under the command of the controller 48.

The operative elements further include first and second pressure sensors 34 and 36; first and second weight scales 38 and 40; and container supports 42 and 44. The operative elements also include a motor-driven driver 46. Operation of all these elements, except the passive supports 42 and 44, is commanded by the controller 48.

Addition details of the structure these operative elements are not essential to the understanding of the invention. However, such additional details are disclosed in copending patent application Ser. No. 08/153,615, U.S. Pat. No. 5,443,451 entitled "Peristaltic Pumping Assembly," filed Nov. 17, 1993 and are incorporated herein by reference.

B. The Blood Processing Set

Figure 3:
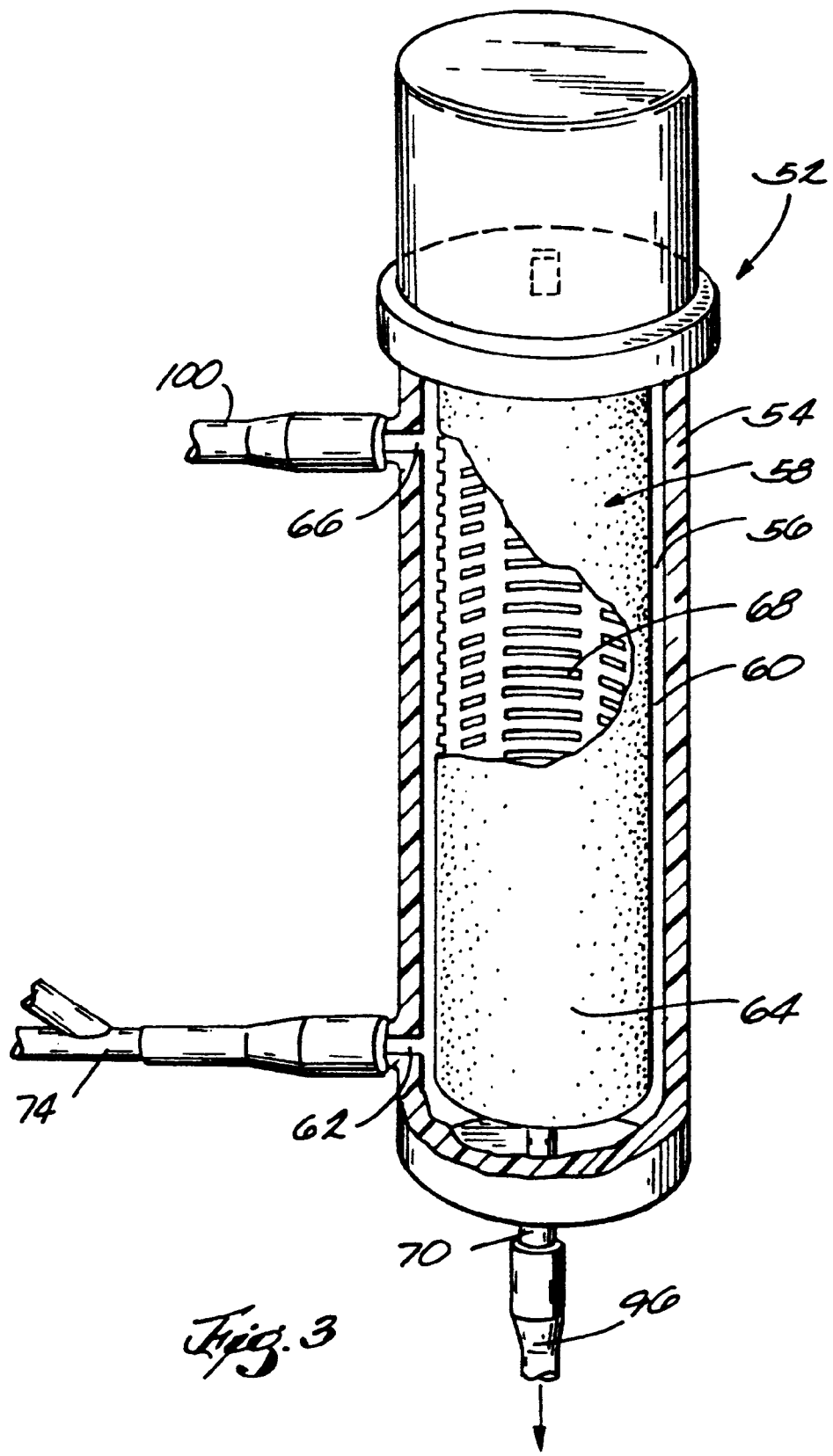
FIG. 3 is a perspective view, partially broken away and in section, of the rotating microporous membrane assembly that forms a part of the disposable blood processing set shown in FIG. 2.

Referring now principally to FIGS. 2 and 3, the blood processing set 14 includes a membrane filtration device 52 that separates whole blood into its cellular and non-cellular components. The device 52 is described and claimed in Fischel U.S. Pat. No. 5,034,135, previously referred to, which is incorporated herein by reference.

The device 52 (see FIG. 3) includes a housing 54 having an interior wall 56. The housing 54 carries an interior rotor or spinner 58. A gap 60 extends between the exterior of the rotor 58 and the housing's interior wall 56. The gap 60 constitutes a zone where blood separation occurs.

In the illustrated embodiment, the gap 60 has a width of about 0.020 inch and a length of about 3.0 inches. An inlet 62 leads into the gap 60 at the bottom of the separation zone.

The rotor 58 carries a microporous membrane 64. The pore size of the membrane 64 is in the range of about 0.4 $\mu$m to 0.8 $\mu$m. The pores of the membrane 64 block passage of the cellular components of whole blood, notably red blood cells, platelets, and leukocytes. The pores of the membrane 64 allow passage of the noncellular plasma constituent of whole blood.

The separated cellular components, which remain in the gap 60, exit the separation zone through a first outlet 66. A series of channels 68 on the rotor 58 behind the membrane 64 carry the noncellular plasma component to a second outlet 70.

Bearings (not shown) carry the rotor 58 for rotation within the housing 54. In use, the housing 54 is mounted on the cabinet 16 (see FIG. 1), where the rotor 58 is magnetically coupled to the driver 46. The driver 46 rotates the rotor 58 at a selected surface velocity. When rotated, the membrane-carrying rotor 58 creates movement of the whole blood in the gap 60. This movement (which takes the form of vortices technically known as Taylor Vortices) induces transport of the cellular components away from the membrane 64 while the noncellular plasma component is transported to the membrane 64 for filtration through the membrane 64. Enhanced membrane separation of plasma from red blood cells (and platelets and leukocytes) occurs.

It should be appreciated that, in an alternative embodiment, the interior wall 56 of the housing 54 could carry the membrane 64. Rotation of the rotor 58 (which, in this alterative embodiment, is free of a membrane) will cause the same vortices to develop and lead to the same enhanced separation results.

Referring back to FIG. 2, the set 14 includes an array of flexible medical grade plastic tubing that conveys fluid into and out of the separation device 52. A first tube 74 carrying a phlebotomy needle 76 communicates with the whole blood inlet 62 of the separation device 52. In use (see FIG. 1), the first tube 74 is strung on the cabinet 16 in operative association with the second peristaltic pump 20. The pump 20 conveys whole blood through the first tube 74 from a donor into the gap 60 for separation. Also in use, the portion of the tube 74 downstream of the pump 20 makes operative contact with the clamp 26. Under the control of the controller 48, the clamp 26 thereby serves to open and close blood flow through the first tube 74.

A first auxiliary branch 78 coupled to the first tube 74 carries a pressure transducer 80 for sensing whole blood pressure downstream of the pump 20. In use (see FIG. 1), the transducer 80 is mounted in operative association with the pressure sensor 34 on the cabinet 16. The sensor 34 monitors the donor's vein pressure, generating an output P1, which will be described in greater detail later.

A second auxiliary branch 82 coupled to the first tube 74 near the inlet 62 carries a pressure transducer 84. In use (see FIG. 1), the transducer 84 is mounted in operative association with the pressure sensor 36 on the cabinet. The sensor 36 thereby monitors whole blood pressure entering the separation gap 60, which closely corresponds with the pressure across the membrane 64, called transmembrane pressure or TMP. The output of the sensor 36 is referred to as P2, which will be described in greater detail later.

A second tube 86 communicates with the first tube 74 near the phlebotomy needle. The second tube 86 carries a conventional spike coupler 88 for connection to a container 90 holding a conventional anticoagulant, like ACD. The second tube 86 also includes an in line drip chamber 92 and sterility filter 96.

In use, the container 90 is hung on the support 42 above the cabinet 16. Also in use (see FIG. 1), the second tube 86 is strung in operative association with the first pump 18. The first pump 18 thereby serves to convey anticoagulant into the whole blood conveyed by the second pump 20. The controller 48 drives the first pump 18 at a prescribed rate relative to the first pump 18 to meter anticoagulant into the whole blood in a set ratio, which is typically about 1 volume part of anticoagulant to 8 to 10 volume parts of whole blood.

A third tube 96 communicates with the second outlet 70 of the separation device 52 to convey plasma from the separation gap 60 to a connected container 98. In the illustrated and preferred embodiment, the container 98 is integrally connected to the third tube 96. In use (see FIG. 1), the third tube 96 is mounted on the cabinet 16 to make operative contact with the clamp 32. The clamp 32 thereby serves to open and close plasma flow through the third tube 96 into the container 98, as commanded by the controller 48. Also in use, the container 98 is hung in association with the weight scale 40. Through the weight scale 40, the controller 48 monitors the volume of plasma collecting in the container 98.

A fourth tube 100 communicates with the first outlet 66 of the separation device 52 to convey red blood cells (with associated platelets and leukocytes) from the separation gap 60 to a connected container 102. In the illustrated and preferred embodiment, the container 102 is integrally connected to the fourth tube 100, which enters at the top of the container 102 (see FIG. 2).

In use (see FIG. 1), the fourth tube 100 is strung in operative association with the third pump 22. The pump 22 thereby serves to convey red blood cells (with associated platelets and leukocytes) from the separation gap 60 to the container 102, as commanded by the controller 48. Also in use, the container 102 is hung in association with the weight scale 38. Through the weight scale 38, the controller 48 monitors the volume of red blood cells collecting in the container 102.

A fifth tube 104 communicates with the container 102. In the illustrated and preferred embodiment, the fifth tube 104 is integrally connected at the bottom of the container 102 (see FIG. 2).

In use (see FIG. 1), the fifth tube 104 is mounted on the cabinet 16 to make operative contact with the clamp 30. The clamp 30 thereby serves to open and close red blood cell flow through the fifth tube 96 from the container 102, as commanded by the controller 48. An auxiliary branch 106 couples the first tube 74 in fluid flow communication with the fifth tube 104 upstream of the clamp 30.

The pump 20 is capable of operation in reverse directions under the direction of the controller 48. The pump 20 thereby serves, when operated in a clockwise direction with the clamp 26 opened and the clamp 30 closed, to draw whole blood from the donor in a first direction through the tube 74 into the separation device 52. When operated in a counter-clockwise direction with the clamp 26 closed and the clamp 30 opened, the pump 20 also serves to draw red blood cells from the container 102 in a reverse direction through tube 74 for return to the donor.

A sixth tube 110 also communicates with the fifth tube 104. The sixth tube 110 carries a conventional spike coupler 112 for connection to a container 114 holding a storage solution for the red blood cells. One such solution is disclosed in Grode et al U.S. Pat. No. 4,267,269. Another such solution is conventionally called "SAG-M" solution. In use (see FIG. 1), the container 114 is hung on the support 44 at the side of the cabinet 16.

The sixth tube 110 also includes an in line filter 116 containing a conventional fibrous filtration medium suited for the removal of leukocytes from red blood cells. The filtration medium can include cotton wool, cellulose acetate or another synthetic fiber like polyester. The filter 116 can be commercially procured, for example, from the Pall Corporation (PALL™ WBF1) or Asahi Medical Company (SEPACELL™ RS2000).

A bypass tube 118 joins the sixth tube 110 upstream and downstream of the filter 116. The bypass tube 118 includes an in line, one-way valve 120 for allowing fluid flow in a direction away from, but not toward, the container 114. The sixth tube 110 also includes a conventional manual roller clamp 122 near the junction of the sixth tube 110. Another conventional manual roller clamp 124 is also present in the sixth tube 110 between the upstream end of the filter 116 and the upstream junction between the sixth tube 110 and bypass tube 118.

A seventh tube 126 communicates with the auxiliary branch 106. The seventh tube 126 carries a conventional spike coupler 128 for connection to a container 130 holding a sterile fluid, like saline. The seventh tube 126 also includes an in line drip chamber 132 and sterility filter 134. In use (see FIG. 1), the container 130 is hung on the support 42 above the cabinet 16, next to the anticoagulant container 90. The seventh tube 126 is also mounted on the cabinet 16 to make operative contact with the clamp 28. The clamp 28 thereby serves to open and close sterile fluid flow from the container 130, as commanded by the controller 48.

The sterile fluid is used to initially prime the disposable set 14 before use. And, as will be described in greater detail later, the sterile fluid can also be used as a replacement fluid conveyed to the donor at certain stages of blood processing.

C. The Controller

Figure 11:
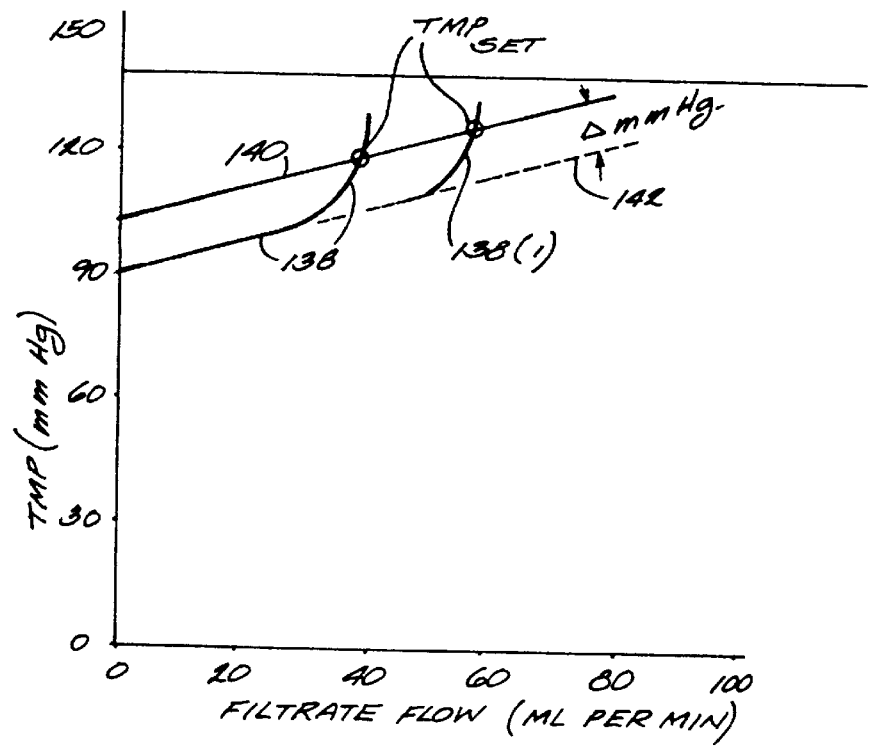
FIG. 11 is a graph showing an enhanced fluid characteristic curve and its intersection with a control curve to establish an elevated set point for transmembrane pressure that optimizes plasma separation efficiency, particularly for lower donor hematocrits.

The flow of plasma filtrate through the outlet 70 will increase linearly as TMP increases, until the TMP forces red blood cells into the membrane 64, blocking it. At this point the TMP rises steeply in a non-linear manner. This relationship between TMP and plasma flow rate defines a fluid characteristic curve for each combination of whole blood flow rate (which is the rate at which the whole blood inlet pump 20 is operated and will be referred to as $RATE_{WB}$), speed of rotation of the rotor 58 (which the controller 48 commands through the driver 46 and will be referred to as ROTOR), and whole blood hematocrit of the donor (which will be referred to as $HCT_{WB}$). FIG. 11 shows a representative fluid charac-teristic curve 138 for one such combination.

Figure 12:
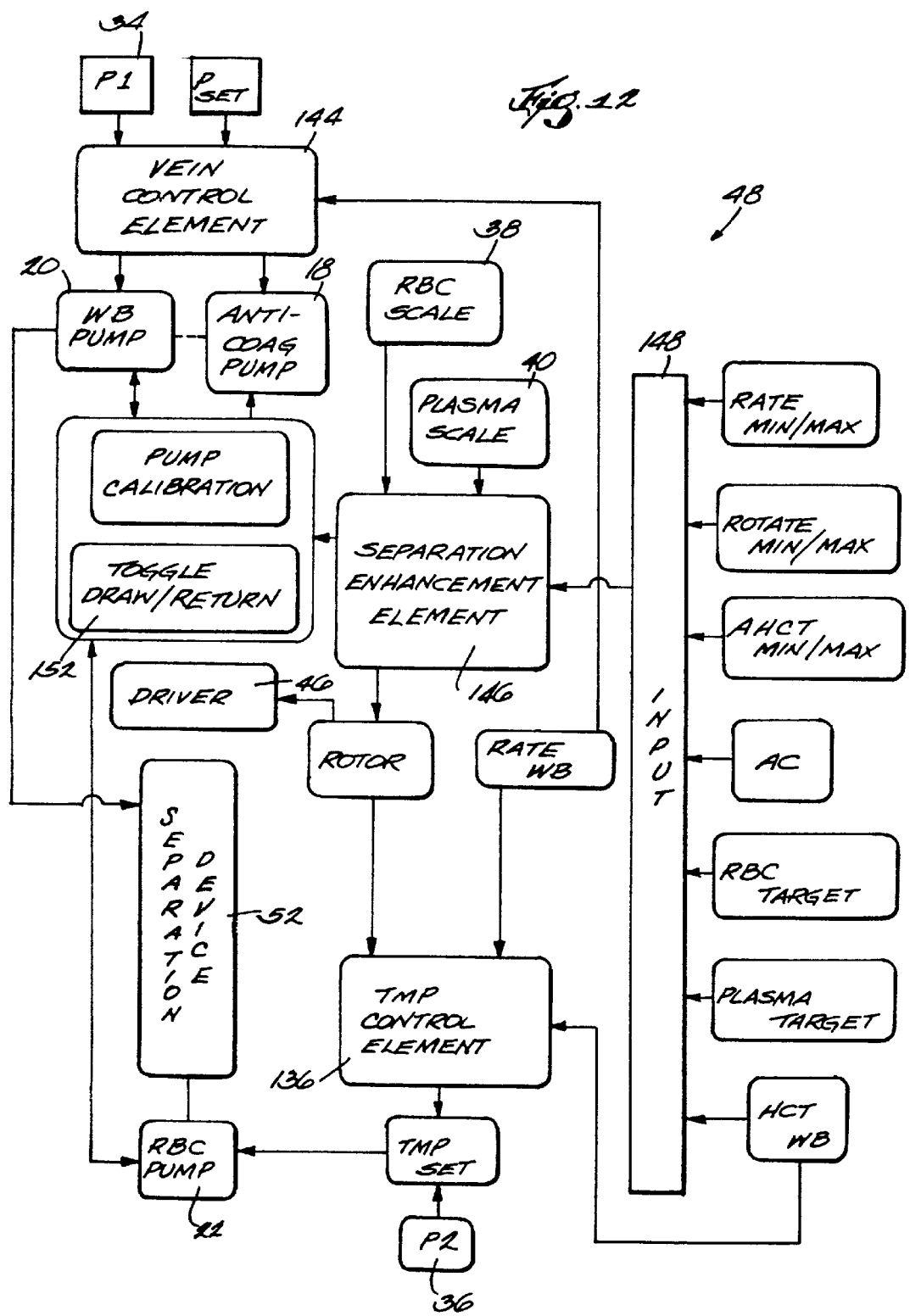
FIG. 12 is a schematic view of the elements of the controller associated with the system shown in FIG. 1, including a separation enhancement element that augments the operation of the TMP control element and vein control element of the controller to separate red blood cells of a uniformly high hematocrit, regardless of donor hematocrit.

As FIG. 12 shows, the controller 48 includes a TMP control element 136. The element 136 monitors pressure P2 sensed by sensor 36 at the whole blood inlet 62 of the separation device 52. As before explained, pressure P2 essential represents the TMP of the separation device 52. The control element 136 compares the sensed TMP to a set TMP (designated $TMP_{SET}$) and varies the pumping rate of the red blood cell pump 22 to stabilize sensed TMP (i.e., P2) at $TMP_{SET}$.

As FIG. 11 shows, $TMP_{SET}$ lies at the intersection of the fluid characteristic curve 138 and a control curve 140. The TMP control element 136 derives the control curve 140 at the outset of every procedure. The control element 136 initially measures P2 at one low filtrate rate and fits a straight line curve having a given slope to the initial sensed point. The slope of the curve, expressed in terms of change of TMP ($\Delta TMP$) over the change in the flow rate of plasma ($\Delta RATE_P$), is a function of the type of microporous membrane 64 used. For example, when the microporous membrane 64 comprises a nylon material, the slope is 26. When the microporous membrane comprises a polycarbonate material, the slope is 13.

In this way, the controller 136 forms a linear prediction curve 142 (shown in phantom lines in FIG. 11). As FIG. 11 shows, the linear portion of the fluid characteristic curve 138 typically follows the slope of the linear prediction curve 142. The TMP control element 136 translates the linear prediction curve 142 upward by a prescribed, empirically determined amount, designated $\Delta$mm Hg in FIG. 11. In the illustrated embodiment, the positive offset $\Delta$mmHg between the linear prediction curve 142 and the control curve 140 is about 24 mm Hg.

Further details of the derivation of the fluid characteristic curve 138 and the control curve 140 are not essential to the invention. These details are set forth in U.S. Pat. No. 4,879,040, which is incorporated herein by reference.

As FIG. 12 also shows, the controller 48 further includes a vein control element 144. The element 144 monitors pressure P1 sensed by sensor 34 downstream of the whole blood pump 20 (see FIG. 4). Pressure P1 essential represents the vein pressure of the donor, which is a negative pressure. A decrease in vein pressure P1 below an empirically determined amount (P1$_{SET}$) indicates the collapse of the phlebotomy vein. The control element 144 continuously compares the sensed P1 with P1$_{SET}$ and varies the pumping rate of the whole blood inlet pump 20 (RATE$_{WB}$) maximize the numerical value of P1 without exceeding the numerical value of P1$_{SET}$.

Further details of the vein control element 144 are not essential to the invention. These details are described in U.S. Pat. No. 4,657,529, which is incorporated herein by reference.

The TMP control element 136 and the vein control element 144 operating as just described will provide plasma separation efficiency (EFF) that varies according to HCT$_{WB}$ as set forth in the following Table 1:

TABLE 1

| HCT$_{WB}$ | EFF | HCT$_{RBC}$ |
|---|---|---|
| 38.5% | 63% | 63% |
| 45% | 56% | 65% |
| 52.5% | 55% | 71% | where:

$$EFF(\%) = \frac{RATE_P}{RATE_{WB} \times (1 - HCT_{WB})} \quad (1)$$

where:
RATE$_P$ is the flow rate of plasma through the outlet 170.
RATE$_{WB}$ is the flow rate of whole blood through the inlet 62.

Table 1 shows that EFF increases as HCT$_{WB}$ decreases. Still, as Table 1 shows, the increase in EFF is not enough at lower HCT$_{WB}$ values to maintain a concentrated red blood cell hematocrit (HCT$_{RBC}$) at or near 70%.

According to the invention, the controller 48 augments the operation of the TMP control element 136 and the vein control element 144 to separate red blood cells suitable for collection and long term storage at high concentrations (i.e., about 70% hematocrit) for all values of HCT$_{WB}$ typically encountered in normal healthy blood donors (i.e., from about 38% hematocrit to about 56% hematocrit and more). At the same time, the controller 48 maintains high plasma separation efficiencies to yield from the same red blood cell donor about 450 ml to 500 ml of plasma suitable for collection, fractionation, or long term storage.

The inventors have discovered that increasing the rotational speed (ROTOR) of the rotor 58 during separation has the effect of extending the linear portion of the fluid characteristic curve without trauma to red blood cells, creating an enhanced fluid characteristic curve 138(1), shown in FIG. 11. As FIG. 11 shows, the new fluid characteristic curve 138(1) intersects the control curve 140 at higher point, resulting in a higher TMP$_{SET}$. Operating at a higher TMP$_{SET}$ results in a higher RATE$_P$ and, therefore, a higher EFF.

The inventors have also discovered that there is a critical interrelationship among HCT$_{WB}$, ROTOR (expressed in revolutions per minute or RPM), and RATE$_{WB}$ (expressed in ml/min) that, in combination with TMP control at TMP$_{SET}$, optimizes EFF to achieve consistent, high HCT$_{RBC}$ for all normal donor HCT$_{WB}$. This interrelationship in effect defines a family of enhanced fluid characteristic curves 138(1) for combinations of HCT$_{WB}$, ROTOR, and RATE$_{WB}$. The intersections of the enhanced fluid characteristic curves 138(1) with the control curve 140 define a family of higher TMP$_{SET}$ points. The higher TMP$_{SET}$ points produce, over the range of normal HCT$_{WB}$, both a consistent, uniform high yield of plasma (about 400 ml to 450 ml) and a likewise consistent, uniform high yield of red blood cells (about 250–275 ml) at a relatively high concentration (HCT$_{RBC}$ of about 70%).

Figure 13:
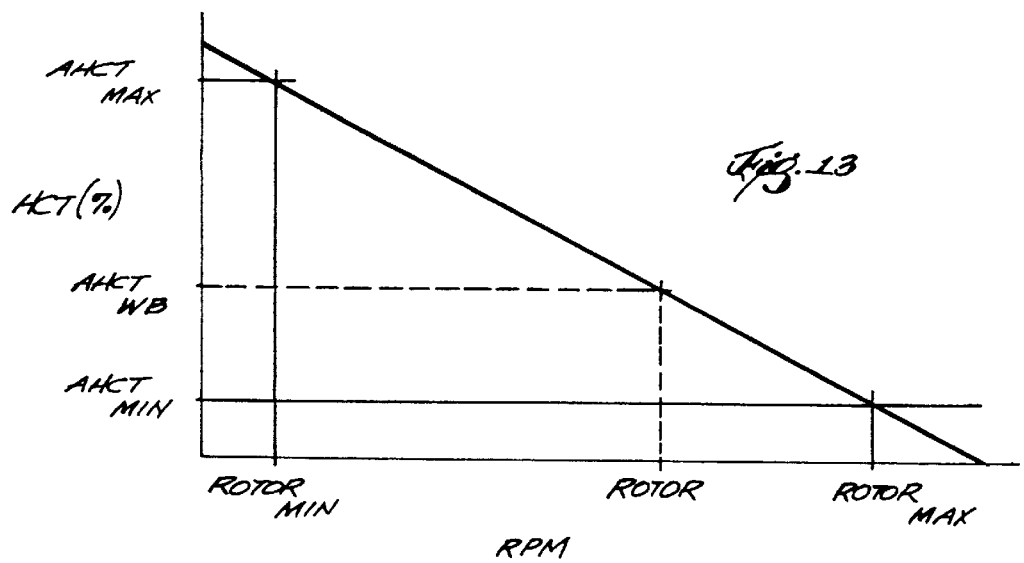
FIG. 13 is a graph showing the relationship between donor hematocrit and the speed of rotation of a rotary membrane separation device that the separation enhancement element of the controller implements to produce red blood cells of a uniformly high hematocrit, regardless of donor hematocrit.

FIG. 13 shows in graphical form the just described relationship discovered between HCT$_{WB}$ and ROTOR for a rotating membrane separation device 52 of the type described above. FIG. 13 demonstrates the general principle, that, as HCT$_{WB}$ decreases, ROTOR must be increased to optimize EFF sufficient to obtain a consistent, uniform high HCT$_{RBC}$. The relationship expressed in the graph in FIG. 13 can be expressed mathematically as follows:

$$\frac{AHCT_{MAX} - AHCT_{WB}}{ROTOR - ROTOR_{MIN}} = \frac{AHCT_{MAX} - AHCT_{MIN}}{ROTOR_{MAX} - ROTOR_{MIN}} \quad (2)$$

where:
AHCT$_{MAX}$ is the maximum anticoagulated hematocrit of whole blood that will be processed. This value is derived as follows:

$$AHCT_{MAX} = HCT_{MAX} \times (1-AC) \quad (3)$$

where:
HCT$_{MAX}$ is the set maximum donor whole blood hematocrit that will be processed. This value is set by the manufacturer taking into account prevailing governmental regulations and clinical experience with the particular separation device 52. For the separation device 52 described above, a nominal value for HCT$_{MAX}$ of about 57 can be used.

AC is the selected anticoagulant ratio. For example, for an anticoagulant ratio of 8%, AC=0.08.

AHCT$_{MIN}$ is the minimum anticoagulated hematocrit of whole blood that will be processed. This value is derived as follows:

$$AHCT_{MAX} = HCT_{MIN} \times (1-AC) \quad (4)$$

where:
HCT$_{MIN}$ is the set minimum donor whole blood hematocrit that will be processed. This value is also set by the operator taking into account prevailing governmental regulations and clinical experience with the particular separation device 52. For the separation device 52 described above, a nominal value for HCT$_{MIN}$ of about 38 can be used.

AHCT$_{WB}$ is the anticoagulated hematocrit of the donor's whole blood entering the separation device 52, derived as follows:

$$AHCT_{WB} = HCT_{WB} \times (1-AC) \quad (5)$$

ROTOR$_{MAX}$ and ROTOR$_{MIN}$ are, respectively, the maximum and minimum rotational speeds set for the rotor 58 for the prescribed range of hematocrits between AHCT$_{MIN}$ and AHCT$_{MAX}$. These speeds are preestablished by the manufacturer, taking into account operational constraints of the driver 46, the separation device 52, and clinical or experimental experience with the separation device 52. $ROTOR_{MAX}$ takes into account clinical or experimental data regarding the onset of clinically significant trauma to cellular components when exposed to the high shear conditions within the rotating membrane separation device 52, given the prescribed range of hematocrits between $AHCT_{MIN}$ and $AHCT_{MAX}$. $ROTOR_{MIN}$ takes into account clinical or experimental data regarding the onset of Taylor Vortex conditions within the gap 60 of the device 52 sufficient to create movement of cellular components away from the rotating membrane 64 while plasma is carried toward the rotating membrane 64 for collection, also given the prescribed range of hematocrits between $AHCT_{MIN}$ and $AHCT_{MAX}$. For the separation device 52 described above, and given the range of minimum and maximum hematocrits of 38% to 56%, nominal values of $ROTOR_{MAX}$=4000 RPM and $ROTOR_{MIN}$=3600 RPM can be used.

Solving Equation (2) for ROTOR yields the following expression:

$$ROTOR = ROTOR_{MAX} - \left[\frac{ROTOR_{MAX} - ROTOR_{MIN}}{AHCT_{MAX} - AHCT_{MIN}} \times (AHCT_{WB} - AHCT_{MIN})\right] \quad (6)$$

Figure 14:
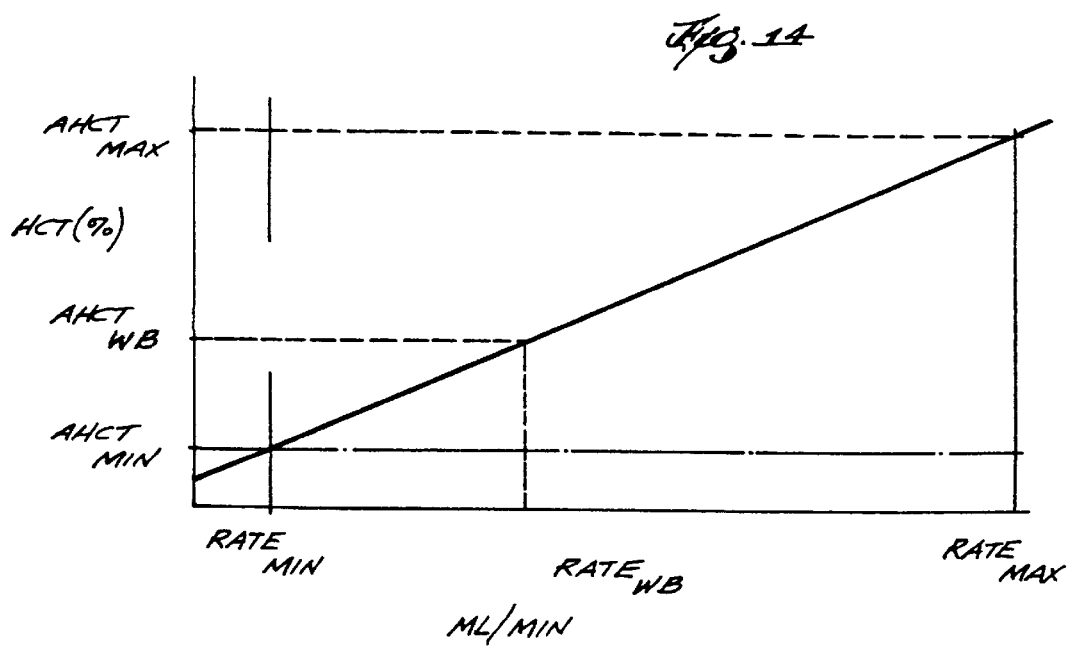
FIG. 14 is a graph showing the relationship between donor hematocrit and the flow rate of whole blood into a rotary membrane separation device that the separation enhancement element of the controller implements to produce red blood cells of a uniformly high hematocrit, regardless of donor hematocrit.

FIG. 14 shows in graphical form the relationship discovered between $HCT_{WB}$ and $RATE_{WB}$ for a rotating membrane separation device 52 of the type described above. FIG. 14 demonstrates the general principle that, as $HCT_{WB}$ increases, $RATE_{WB}$ must be increased to optimize EFF sufficient to obtain a consistent, uniform high $HCT_{RBC}$. This is because (see Equation (1)), as $RATE_{WB}$ decreases, EFF is increased, as long as other operating conditions remain the same.

It is necessary to consider both the relationship between $HCT_{WB}$ and $RATE_{WB}$ and the relationship between $HCT_{WB}$ and ROTOR at the same time. This is because, as $HCT_{WB}$ decreases, it is not always possible to increase ROTOR high enough to alone optimize EFF because of the constraints imposed by $ROTOR_{MAX}$ and $AHCT_{MAX\ or\ MIN}$.

The relationship expressed in the graph in FIG. 14 can be expressed mathematically and solved for $RATE_{WB}$, as follows:

$$RATE_{WB} = \left[\frac{RATE_{MAX} - RATE_{MIN}}{AHCT_{MAX} - AHCT_{MIN}} \times (AHCT_{WB} - AHCT_{MIN})\right] + RATE_{MIN} \quad (7)$$

where:

$RATE_{MAX}$ and $RATE_{MIN}$ are, respectively, the maximum and minimum flow rates (expressed in ml/min) set for the pump 20, taking into account $AHCT_{MAX}$ and $AHCT_{MIN}$. These flow rates are established by the manufacturer taking into account operational constraints of the pump 20 and clinical or experimental experience. $RATE_{MIN}$ takes into account, given the prescribed range of minimum and maximum hematocrits, minimum flow rate conditions required for effective separation conditions in the separation device 52 without unduly prolonging exposure to the blood to the high shear conditions present within the gap 60, thereby causing trauma. $RATE_{MAX}$ takes into account, also given the prescribed range of minimum and maximum hematocrits, maximum flow rates of drawing whole blood from a typical donor without causing discomfort or experiencing vein collapse. For the separation device 52 described above, and given the range of minimum and maximum hematocrits of 38% to 56%, nominal values of $RATE_{MAX}$=100 ml/min and $RATE_{MIN}$=80 ml/min can be used.

According to the invention, the controller 48 includes a separation enhancement element 146 (see FIG. 12) that augments the operation of the TMP control element 136 and the vein control element 144, by taking into account the interrelationships described above among $HCT_{WB}$, ROTOR, and $RATE_{WB}$.

The separation enhancement element 146 includes an input 148 that receives from the operator the value of $HCT_{WB}$ for the individual donor whose blood is to be collected. The input 148 also receives from the donor the selected anticoagulant ratio AC. From these, the separation enhancement element 146 calculates $AHCT_{WB}$, using Equation (5). The input 148 receives also receives the targeted red blood cell collection volume ($RBC_{Target}$) and the targeted plasma collection volume ($PLASMA_{Target}$) from the operator at the outset of a given procedure. The input 148 can comprise touch pad entry keys 150 on the device 12 (as FIG. 1 shows).

The separation enhancement element 146 includes in manufacturer-installed memory the prevailing set operating parameters $RATE_{MAX\ and\ MIN}$; $ROTOR_{MAX\ and\ MIN}$; and $AHCT_{MAX\ and\ MIN}$.

From this input, the separation enhancement element 146 derives ROTOR according to the relationships expressed in Equation (6). The separation enhancement element 146 also derives from this input $RATE_{WB}$ according to the relationships expressed in Equation (7).

The separation enhancement element 146 commands the TMP control element 136 to derived $TMP_{SET}$ using the enhanced fluid characteristic curve 138(1) that the particular combination of $HCT_{WB}$; ROTOR; and $RATE_{WB}$ defines.

The separation enhancement element 146 also commands the driver 46 to spin the rotor 58 at ROTOR. The construct of Equation (6) assures that $ROTOR_{MIN} \leq ROTOR \leq ROTOR_{MAX}$.

The separation enhancement element also commands the vein control element 144 to maintain pump 20 at $RATE_{WB}$. The construct of Equation (7) assures that $RATE_{MIN} \leq RATE_{WB} \leq RATE_{MAX}$.

The vein control element 144 controls the pump 20 at $RATE_{WB}$, unless sensed P1<$P_{SET}$, indicating a vein collapse condition. In this instance, the vein control element 144 reduces $RATE_{WB}$ by a prescribed percentage increment (for example, by 5% of $RATE_{WB}$). The vein control element 144 also commands the driver 46 to reduce ROTOR based upon functions of Equations (6) and Equation (7), as the family of curves shown in FIG. 15 demonstrate.

Figure 15:
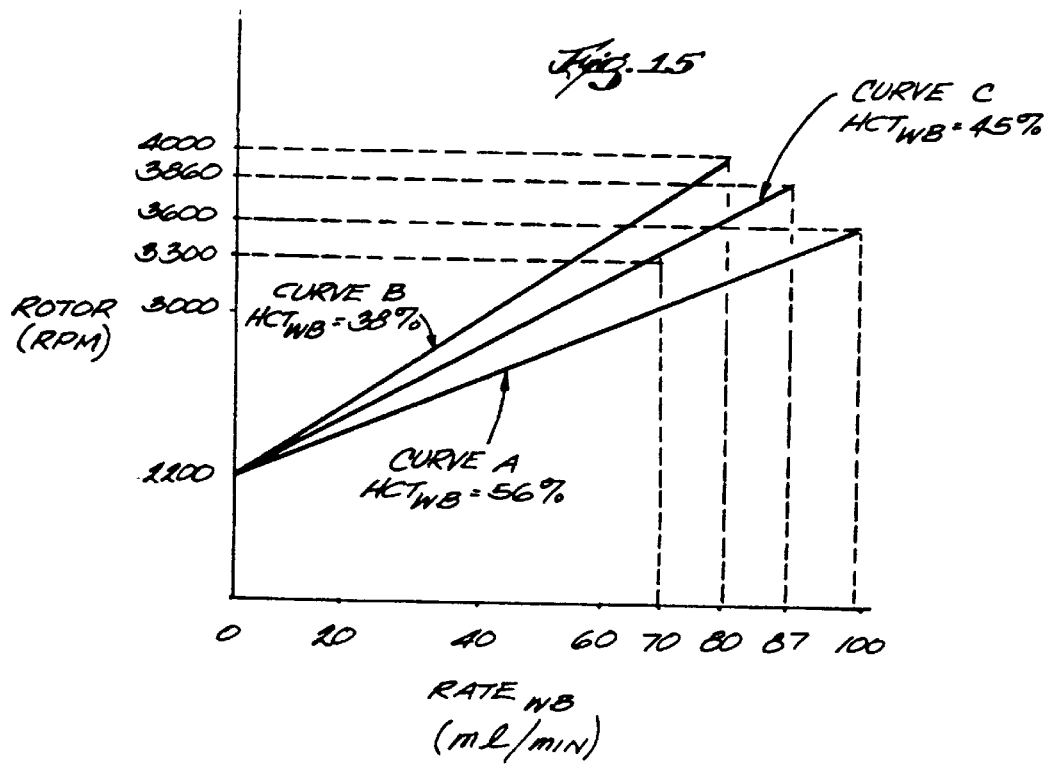
FIG. 15 shows a family of curves showing the relationship between donor hematocrit, the speed of rotation of the rotary membrane separation device, and the flow rate of whole blood, which is used by the vein control element to control the speed of rotation when a collapsed vein condition is detected, requiring a reduction of the flow rate of whole blood.

The x-axis of FIG. 15 shows $RATE_{WB}$ (in ml/min) increasing from the lowest possible flow rate ($RATE_{WB}$=0) to the maximum possible blood flow rate $RATE_{WB}$ prescribed according to the function expressed by Equation (7), given a $HCT_{WB}$ falling within the prescribed range of minimum and maximum hematocrits of 38% to 56%, and given the prescribed $RATE_{MAX}$ and $RATE_{MIN}$.

The y-axis of FIG. 15 shows ROTOR increasing from a prescribed minimum possible rotational rate permitted at $RATE_{WB}$=0 (which, for the device 54 described above, is set at 2200 RPM) to the maximum possible rotation rate ROTOR prescribed according to the function expressed in Equation (6), given a $HCT_{WB}$ again falling within the prescribed range of minimum and maximum hematocrits of 38% to 56%, and given the prescribed $ROTOR_{MAX}$ and $ROTOR_{MIN}$.

From this, a family of curves setting $RATE_{WB}$ as a function of ROTOR for a given $HCT_{WB}$ and can be drawn, three of which (Curves A, B, and C) are shown in FIG. 15. Curve A represents the $RATE_{WB}$/ROTOR function for maximum $HCT_{WB}$=56%, extending from the intersection of $RATE_{WB}$=0/ROTOR=2200 to the intersection of $RATE_{WB}$=100 ml/min (derived by Equation (7))/ROTOR=3600 RPM (derived by Equation (6). Curve B represents the $RATE_{WB}$/ROTOR function for minimum $HCT_{WB}$=38%, extending from the intersection of $RATE_{WB}$=0/ROTOR=2200 to the intersection of $RATE_{WB}$=80 ml/min (derived by Equation (7))/ROTOR=4000 RPM (derived by Equation (6). Curve C represents the $RATE_{WB}$/ROTOR function for an intermediate (and typical) hematocrit value $HCT_{WB}$=45%, extending from the intersection of $RATE_{WB}$=0/ROTOR=2200 to the intersection of $RATE_{WB}$=87 ml/min (derived by Equation (7))/ROTOR=3860 RPM (derived by Equation (6).

Based upon the FIG. 15 family of curves, and given $HCT_{WB}$ and the incrementally reduced $RATE_{WB}$, the vein control element 144 derives ROTOR. For example, if $HCT_{WB}$=45%, and the incrementally reduced $RATE_{WB}$=70 ml/min, ROTOR=3300 RPM.

If sensed P1 continues to indicate a vein collapse condition, the vein control element 144 makes another incremental decrease to the pump rate and adjustment to the rate of rotation, as above described, and so on until the collapsed vein condition is eliminated. The vein control element 144 then proceeds to incrementally increase the pump rate and adjust the speed of rotation over time, as above described, to seek to return the pump rate to $RATE_{WB}$ and the rotor driver rate to ROTOR, or as close to these prescribed conditions that P1 will allow.

The vein control element 144 also controls the pump 18 in synchrony with the pump 20 to assure that the desired anticoagulant ratio AC is maintained.

Meanwhile, the TMP control element 136 senses P2 and commands the pump 22 at a $RATE_{RBC}$ that will maintain P2=$TMP_{SET}$.

Concurrent with the operation of the TMP control element 136 and vein control element 144 as just described, the separation enhancement element 146 receives input from the weight scales 38 and 40, relating to the volumes of concentrated red blood cells and plasma being collected. The element 146 commands a toggle control element 152 based upon this input, the $RBC_{Target}$, and the $PLASMA_{Target}$ specified by the operator. The element 152 toggles the system 10 between operation in successive blood draw modes and blood return modes, consistent with conventional single needle procedures.

During the blood draw mode, the system 10 operates the pump 20 in the forward direction to draw whole blood from the donor for separation into red blood cells, which collect in the container 102, and plasma, which collects in the container 98. After a first prescribed volume of concentrated red blood cells is processed, the separation enhancement element 146 commands the element 152 to switch the system 10 to a return mode. During the return mode, the system 10 operates the pump 20 in the reverse direction to draw concentrated red blood cells from the container 102 for return to the donor. The separation enhancement element 146 compares collected plasma and red blood cell volumes to $RBC_{Target}$ and $PLASMA_{Target}$ and derives a second prescribed volume of whole blood to be processed. The separation enhancement element 146 then commands the element 152 to switch the system 10 back to a draw mode to collect this prescribed volume. The separation enhancement element 146 continues to command toggling between successive draw and return modes, while monitoring the weight scales 38 and 40, until $RBC_{Target}$ and $PLASMA_{Target}$ are achieved.

In the illustrated and preferred embodiment, while red blood cells collect in the container 102, the separation enhancement element 146 also samples the output of the weight scale 38 over time. The separation enhancement element 146 derives the actual flow rate $RATE_{RBC-Real}$ of red blood cells into the container by the change in container 102 weight over time. The separation enhancement element 146 compares $RATE_{RBC-REAL}$ to $RATE_{RBC}$ commanded by the TMP control element 136 and derives a difference, if any. The separation enhancement element 146 periodically issues adjustment commands to the pump 22 based upon the difference to assure that $RATE_{RBC-Real}$ corresponds to the command $RATE_{RBC}$ issued by the TMP control element 136.

Likewise, in the illustrated and preferred embodiment, while plasma collects in the container 98, the separation enhancement element 146 samples the output of weight scale 40 over time. The separation enhancement element 146 derives the actual flow rates of plasma $RATE_{PLASMA-Real}$ of plasma into the container 98 by the change in container 98 weight over time. The separation enhancement element 146 adds $RATE_{PLASMA-Real}$ and $RATE_{RBC-REAL}$ to derive $RATE_{WB-Real}$. Alternatively, the separation enhancement element 146 can convert $RATE_{RBC-Real}$ into $RATE_{WB-Real}$, without using the weight scale 40 output to derive $RATE_{PLASMA-Real}$, as follows:

$$RATE_{WB-Real} = RATE_{RBC-Real} + \frac{(1 - HCT_{WB})}{HCT_{WB}} RATE_{RBC-Real} \qquad (8)$$

The separation enhancement element 146 compares the derived $RATE_{WB-Real}$ to $RATE_{WB}$ commanded by the vein control element 144 (as above described) and derives a difference, if any. The separation enhancement element 146 periodically issues adjustment commands to the pump 20 based upon the difference to assure that $RATE_{WB-Real}$ corresponds with the command $RATE_{WB}$ issued by the vein control element 136.

EXAMPLE 1

FIGS. 4 to 9 and Table 2 exemplify the operation of the system shown in FIGS. 1 to 3 under the control of the controller 48 in a manner that embodies the features of the invention.

In this Example, a rotating membrane separation device of the type and dimensions describe above is used. In this Example, the operator enters the following prescribed condition inputs to the separation enhancement element 146:

$HCT_{WB}$=46 (%)
$RBC_{Target}$=250 ml
$PLASMA_{Target}$=475 ml
$RATE_{MAX}$=100 ml/min
$RATE_{MIN}$=80 ml/min
$ROTOR_{MAX}$=4000 RPM
$ROTOR_{MIN}$=3600 RPM
$AHCT_{MAX}$=56 (%)
$AHCT_{MIN}$=38 (%)
AC=8 (%)

Based upon this input, the separation enhancement element 146 derives
ROTOR=3835 RPM
$RATE_{WB}$=88 ml/min At the beginning of the procedure, the TMP control element 136 derives $TMP_{SET}$ and the vein control element 144 sets $P_{SET}$.

The separation enhancement element 146 commands three successive draw/return cycles. The following Table 2 summarizes the blood volumes and times for the three cycles.

TABLE 2

| CYCLE | WHOLE BLOOD VOLUME (ML) | RED BLOOD CELL VOLUME (ML) | PLASMA VOLUME (ML) | SALINE VOLUME (ML) | TIME (MIN) |
|---|---|---|---|---|---|
| 1. DRAW | 451 | 275 | 148 | | 5.26 Note: 28 ml constitutes residual priming volume |
| RETURN | 0 | −275 | 0 | 0 | 2.11 |
| 2. DRAW | 473 | 275 | 198 | 0 | 5.26 |
| RETURN (SALINE) | 0 | 0 | 0 | 240 | 1.85 |
| RETURN (RED BLOOD CELLS) | 0 | −179 | 0 | 0 | 1.38 |
| 3. DRAW | 308 | 179 | 129 | 0 | 3.42 |
| RETURN | 0 | −25 | 0 | 0 | .19 |
| TOTALS | 1232 | 250 | 475 | 240 | 19.47 |

Figure 4:
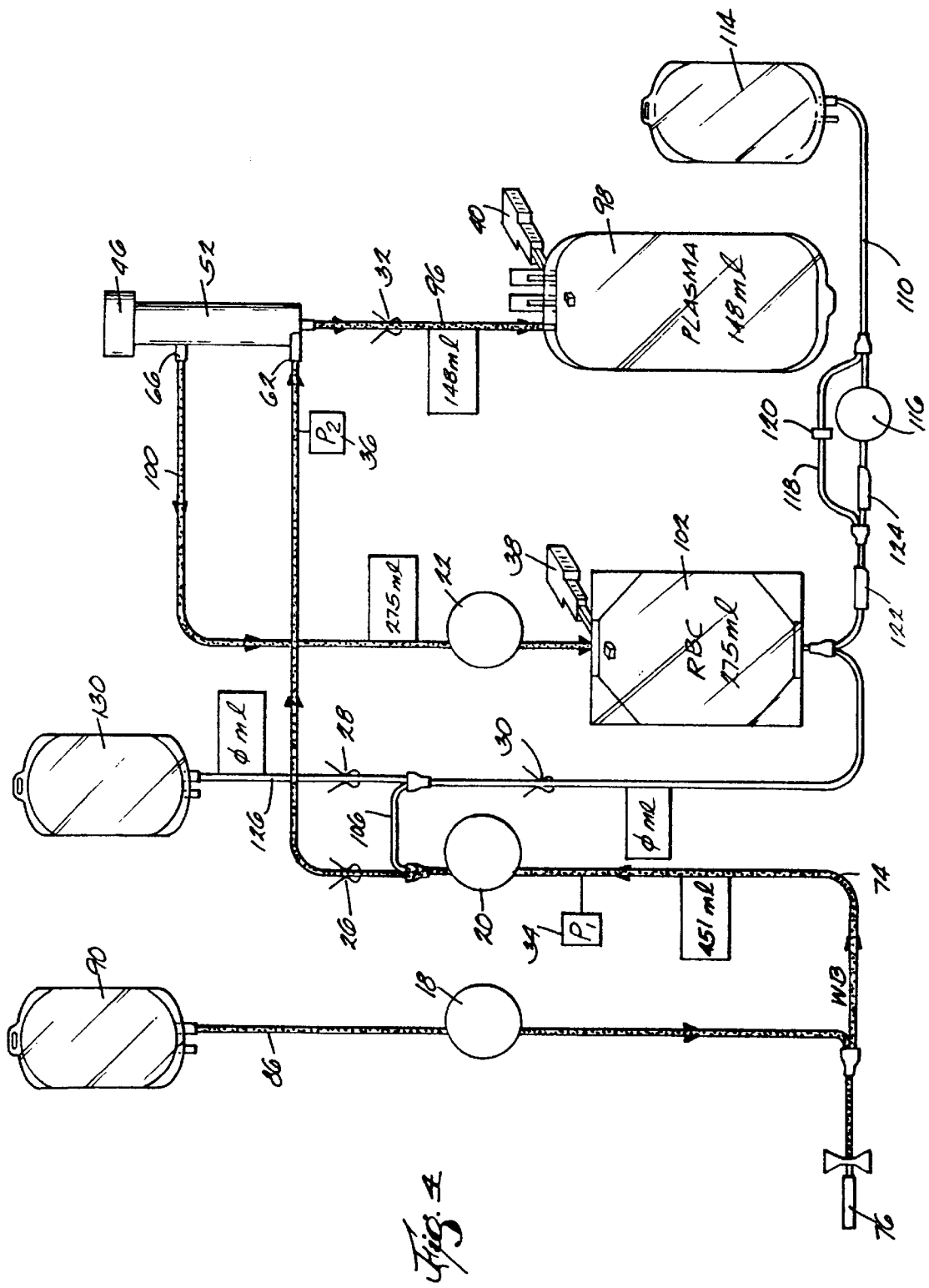
FIG. 4 is a schematic view of the blood collection system shown in FIG. 1 being operated in a first draw cycle.
Figure 5:
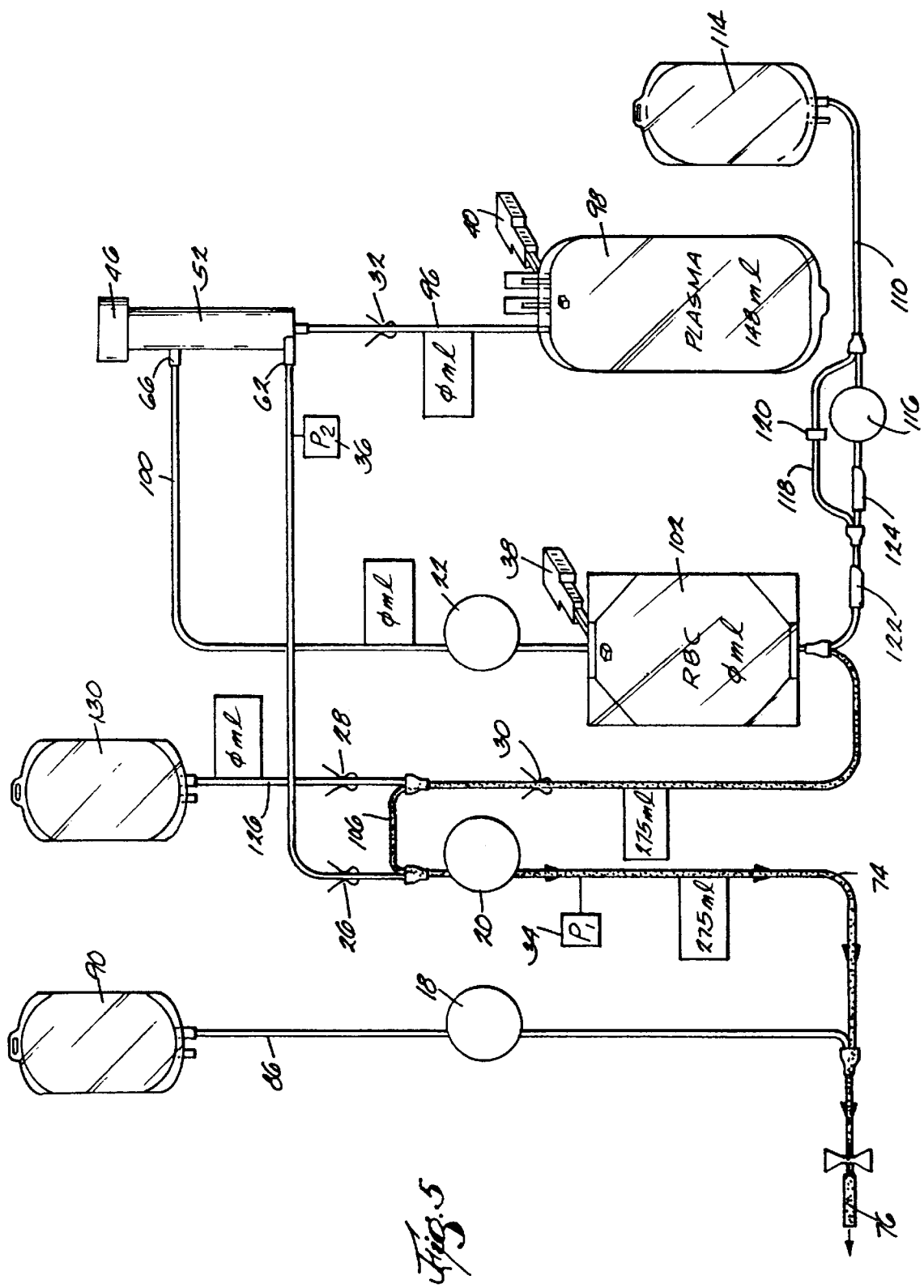
FIG. 5 is a schematic view of the blood collection system shown in FIG. 1 being operated in a first return cycle.

FIG. 4 schematically shows fluid flow and associated fluid volumes using the Cycle 1 draw mode. FIG. 5 schematically shows fluid flow and associated fluid flow volumes during the Cycle 1 return mode.

Figure 6:
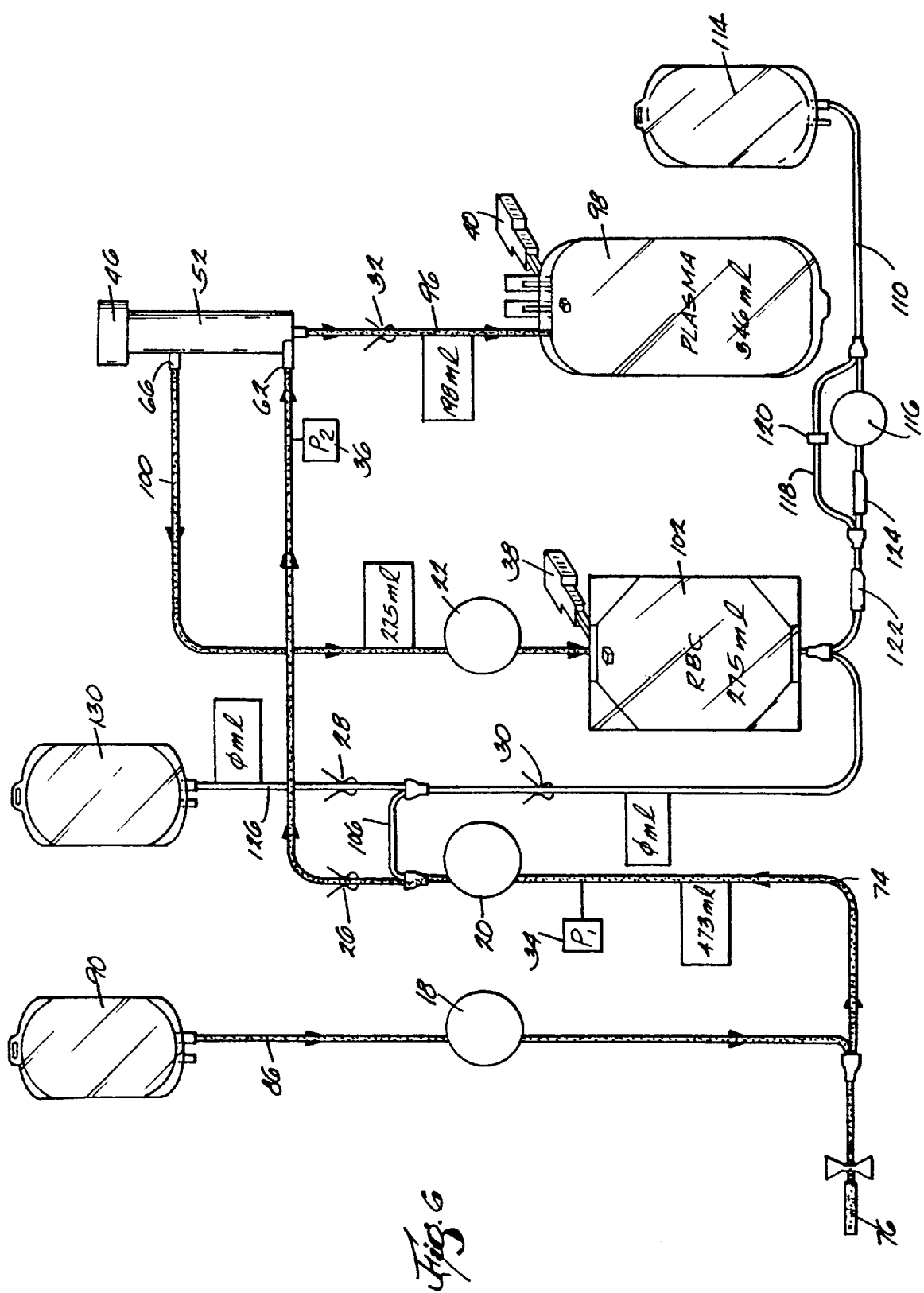
FIG. 6 is a schematic view of the blood collection system shown in FIG. 1 being operated in a second draw cycle.
Figure 7:
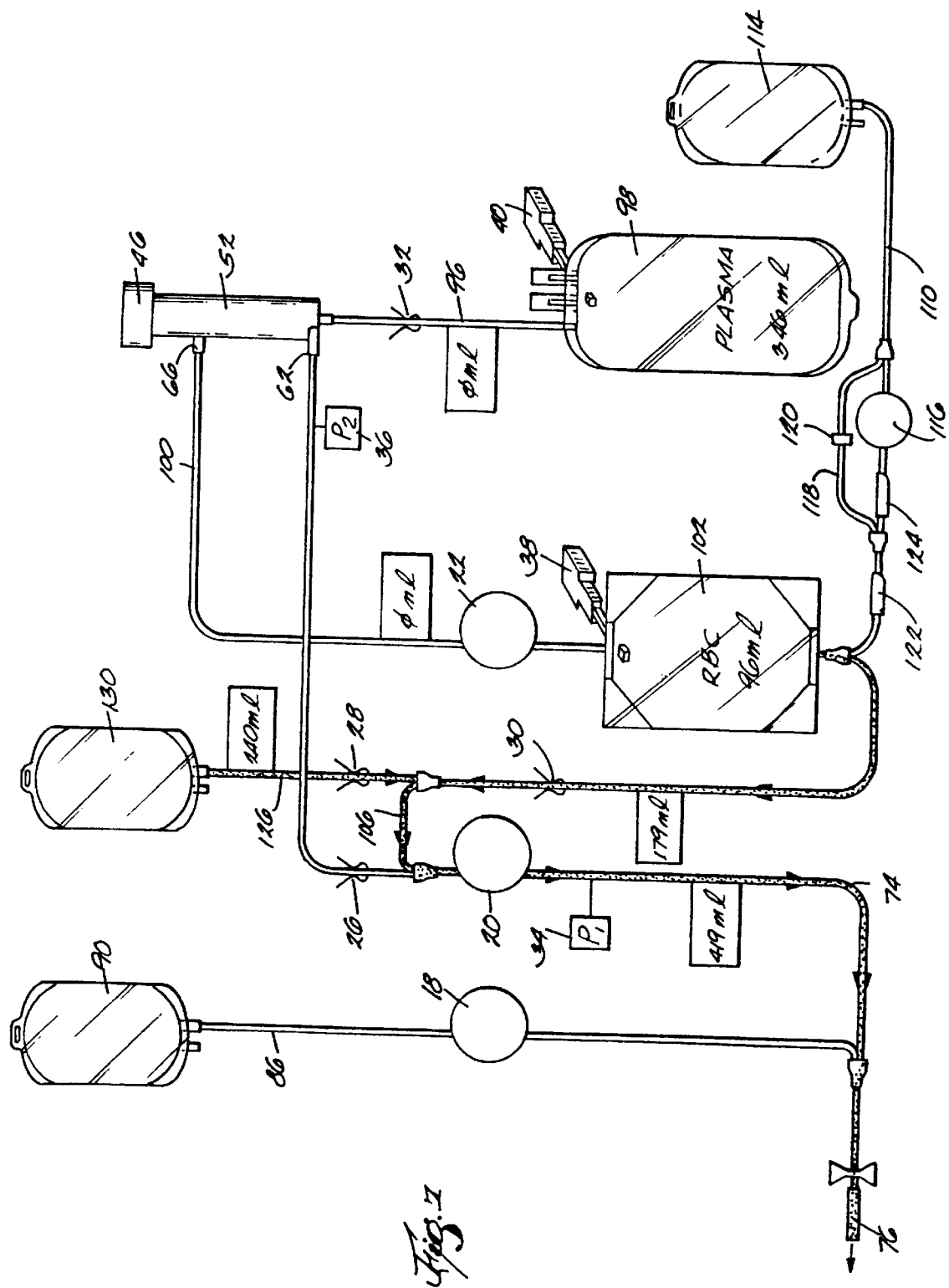
FIG. 7 is a schematic view of the blood collection system shown in FIG. 1 being operated in a second return cycle.

FIG. 6 schematically shows fluid flow and associated fluid flow volumes during the Cycle 2 draw mode. FIG. 7 schematically shows fluid flow and associated fluid flow volumes during the Cycle 2 return mode, during which red blood cells and saline are sequentially returned to the donor, with saline being returned first, followed by red blood cells.

Figure 8:
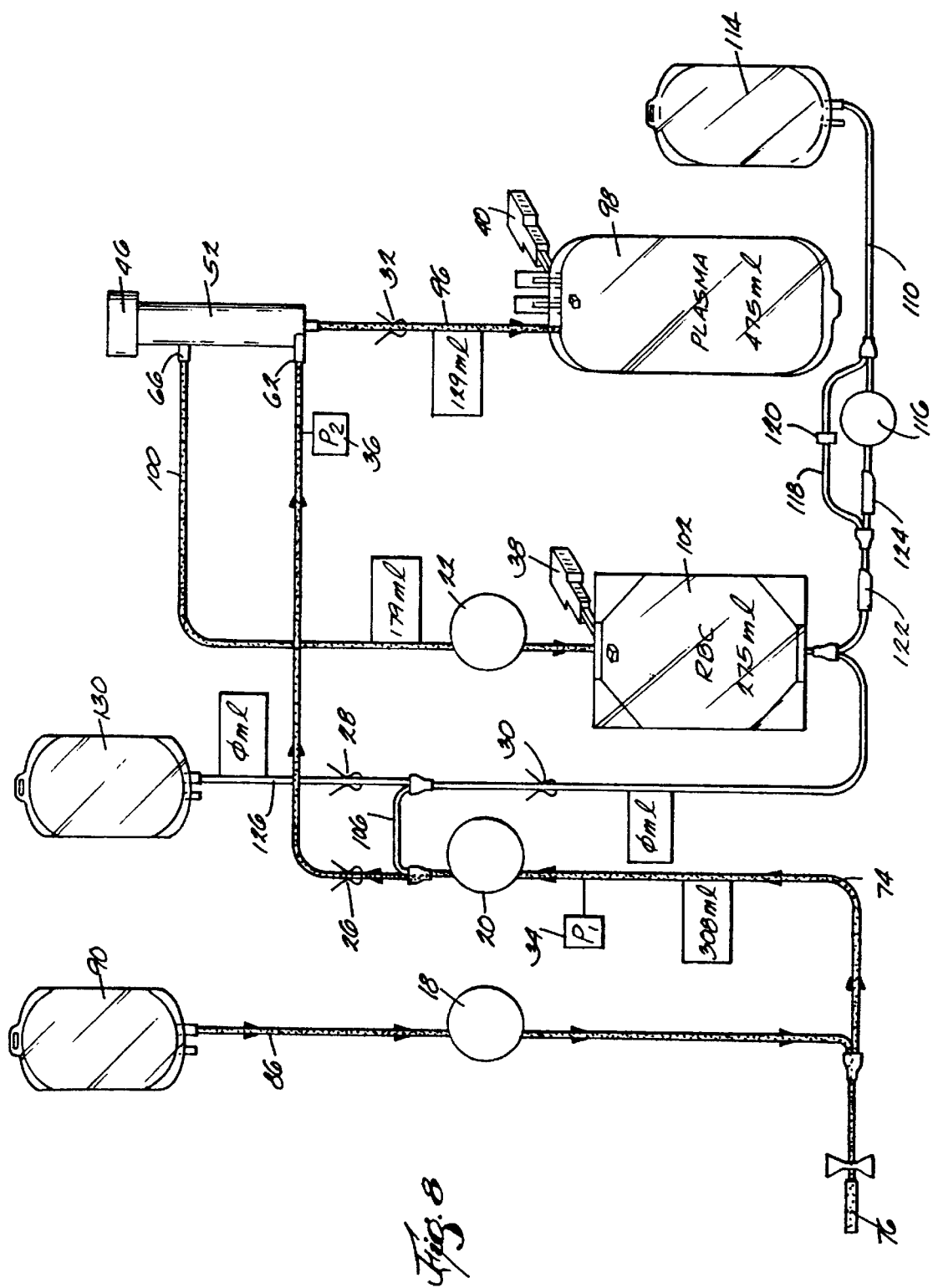
FIG. 8 is a schematic view of the blood collection system shown in FIG. 1 being operated in a third and final draw cycle.
Figure 9:
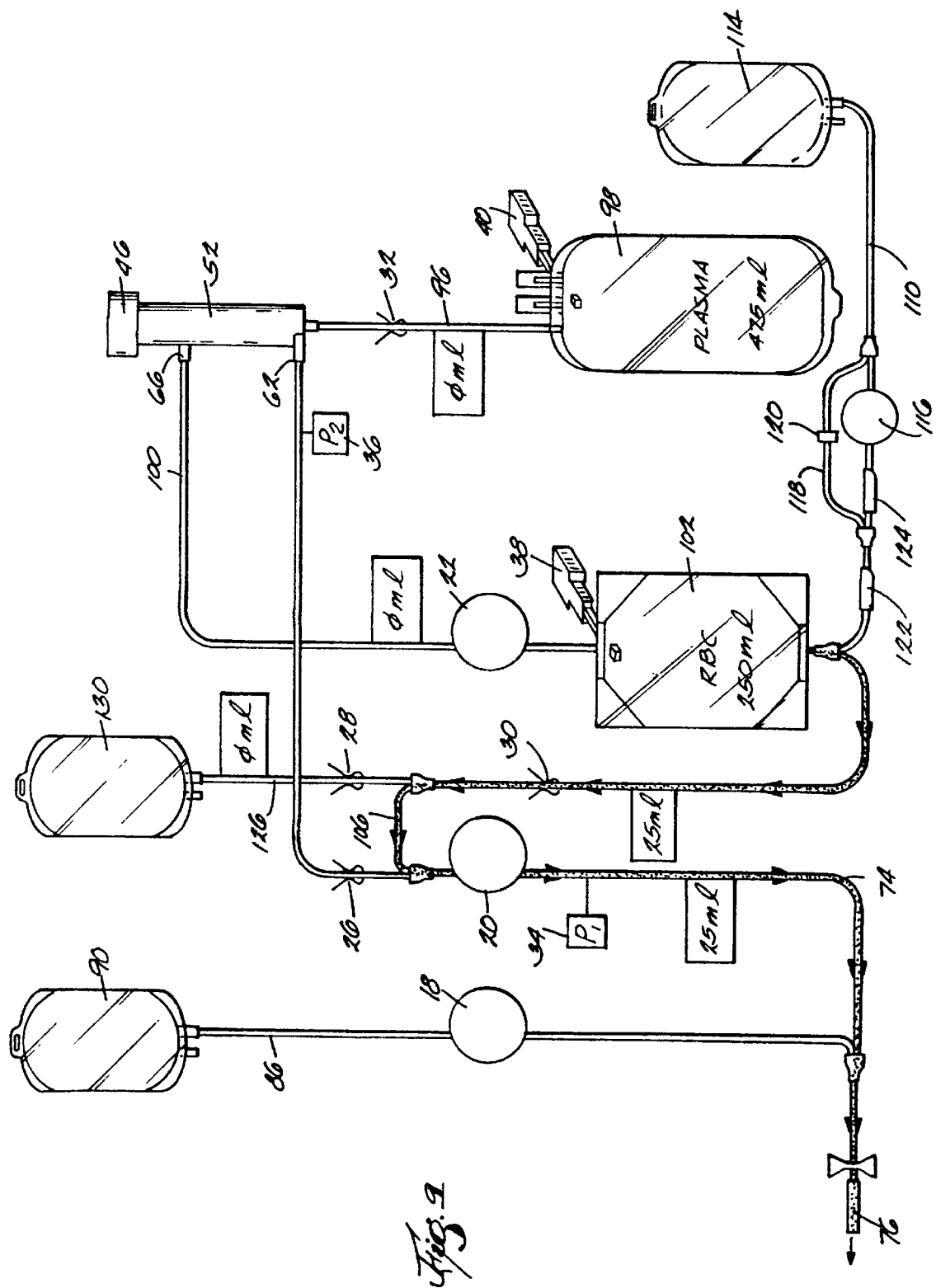
FIG. 9 is a schematic view of the blood collection system shown in FIG. 1 being operated in a third and final return cycle.

FIG. 8 schematically shows fluid flow and associated fluid flow volumes during the Cycle 3 draw mode. FIG. 9 schematically shows fluid flow and associated fluid flow volumes during the Cycle 3 final return mode.

D. Leukoreduction of Collected Red Blood Cells

In the illustrated and preferred embodiment (see FIG. 2), the set 14 includes a leukoreduction filter 116, as previously described. FIGS. 10A and B show the sequence of using the filter 116 to remove leukocytes from the concentrated red blood cells collecting the preceding Example. The sequence is performed manually, after the donor has been disconnected from the system 10.

The operator first opens the roller clamp 122. The operator takes the container 114 off the support 44 and lifts it above the container 102. The operator transfers by gravity flow the storage solution from the container 114 (as FIG. 10A shows), through the bypass path 118 with the one-way valve 120 and the sixth and fifth tubes 110/104 into the red blood cells in the container 102 (which is still preferable supported on the weight scale 38 at this time). The operator preferably returns the container 114 (now empty) to the support 44. The container 102 now contains the volume of collected red blood cells and the additional volume of storage solution (indicated as 250 ml(+) in FIG. 10A).

Figure 10B:
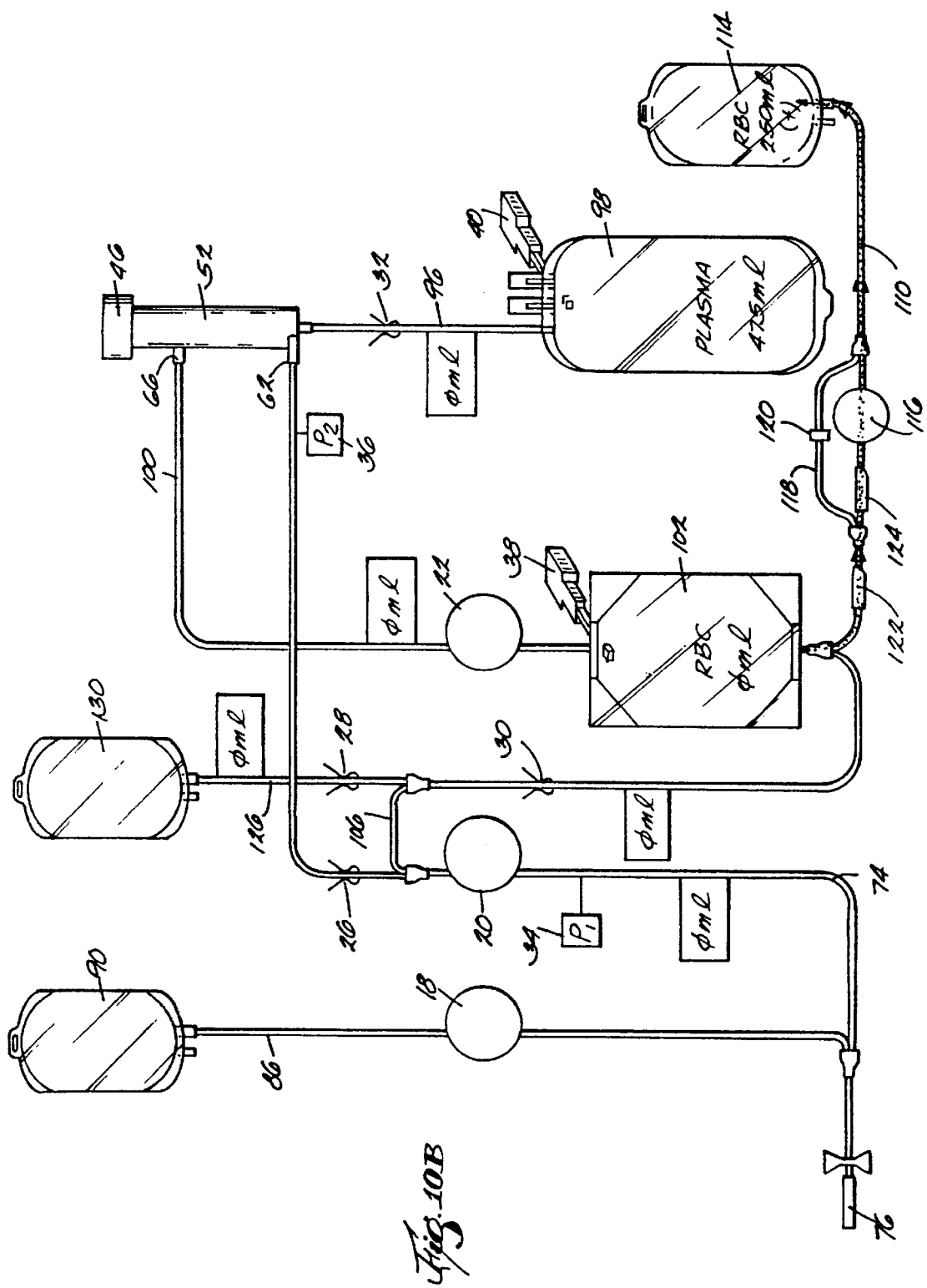
FIGS. 10A and B are schematic views of the blood collection system shown in FIG. 1 being manipulated to remove leukocytes from the concentrated red blood cells before storage.

The operator takes the container 102 off the weight scale 38 and gently squeezes the container 102 to mix the red blood cells with the storage solution in the container 102. The operator then opens the roller clamp 124 and lifts the container 102 above the container 114 (now on the support 44). Red blood cells and storage solution flow through the fifth tube 104, sixth tube 110, and through the filter 116 into the container 114 (as FIG. 10B shows). Leukocytes are thereby removed from the red blood cells.

The leukocyte-reduced red blood cells and resident storage solution are retained in the container 114 for long term storage. The container 114 holds the collected volume of red blood cells plus the additional volume of storage solution (designated 250 ml(+) in FIG. 10B). The collected volume of plasma is likewise retained in the container 98 for storage or further processing. The containers 114 and 98, along with the other containers and tubing associated with the set 14, are made from conventional approved medical grade plastic materials, such as polyvinyl chloride plasticized with di-2-ethylhexyl-phthalate (DEHP). Containers made from such materials are known to demonstrate characteristics beneficial to the storage of either red blood cells or plasma for at least twenty-four hours after separation, for subsequent transfusion or processing.

The containers 114 and 98, with the blood components they hold, are separated from the set 14 by forming snap-apart seals in the tubes 104, 100, and 110, using, for example, a conventional heat sealing device like the Hematron® dielectric sealer sold by Baxter Healthcare Corporation.

The inventors have further discovered that red blood cells processed in the rotating membrane separating device 52 and collected according to the invention in high hematocrit concentrations, demonstrate significantly lower hemolysis levels before and after long term storage in a leukocyte-reduced condition, compared to comparable high hematocrit concentrations collected according to the invention in which the population of leukocytes is not reduced. The following Table 3 summarizes the difference of hemoglobin levels under such conditions using commercially available leukocyte filters (Filter 1=PALL™ WBF1 and Filter 2=Asahi SEPACELL™ RS2000).

TABLE 3

| | Collected Using System 10 With Pre-Storage Leukoreduction (Filter 1)* | Collected Using System 10 with Pre-Storage Leukoreduction (Filter 2)* | Collected Using System 10 Without Pre-Storage Leuko-Reduction | Manually Collected Unfiltered Red Blood Cells |
|---|---|---|---|---|
| Avg $HCT_{RBC}$ | 68.7% | 69.4% | Comparable to foregoing columns | Typically about 70% |
| Measured Hemolysis (%) Storage Day 0** (10 Samples) | 0.08% ± 0.02 | 0.06% ± 0.01 | about 0.13% | Typically about 0.08% |
| Measured Hemolysis (%) Storage Day 42** (Same 10 Samples) | 0.30% ± 0.04 | 0.36% ± 0.17 | about 0.82% | Typically about 0.56% |

*Note: Both Filter 1 and Filter 2 reduced leukocyte (white blood cell) levels below $1 \times 10^5$.
**Note: The red blood cell concentrations were stored in association with ADSOL ® Storage Media, sold by Baxter Healthcare Corporation.

Table 3 shows acceptable hemolysis levels exist in high concentrated red blood cell products collected according to the invention (columns 1 to 3). Table 3 also demonstrates that reducing the number of leukocytes from the highly concentrated red blood cell products reduces the hemolysis levels both at the outset of storage and at the end of the storage period (columns 1 and 2), compared to highly concentrated red blood cells products that were not leuko-reduced before storage (column 3).

II. Batch Processing Systems and Methods

Figure 16:
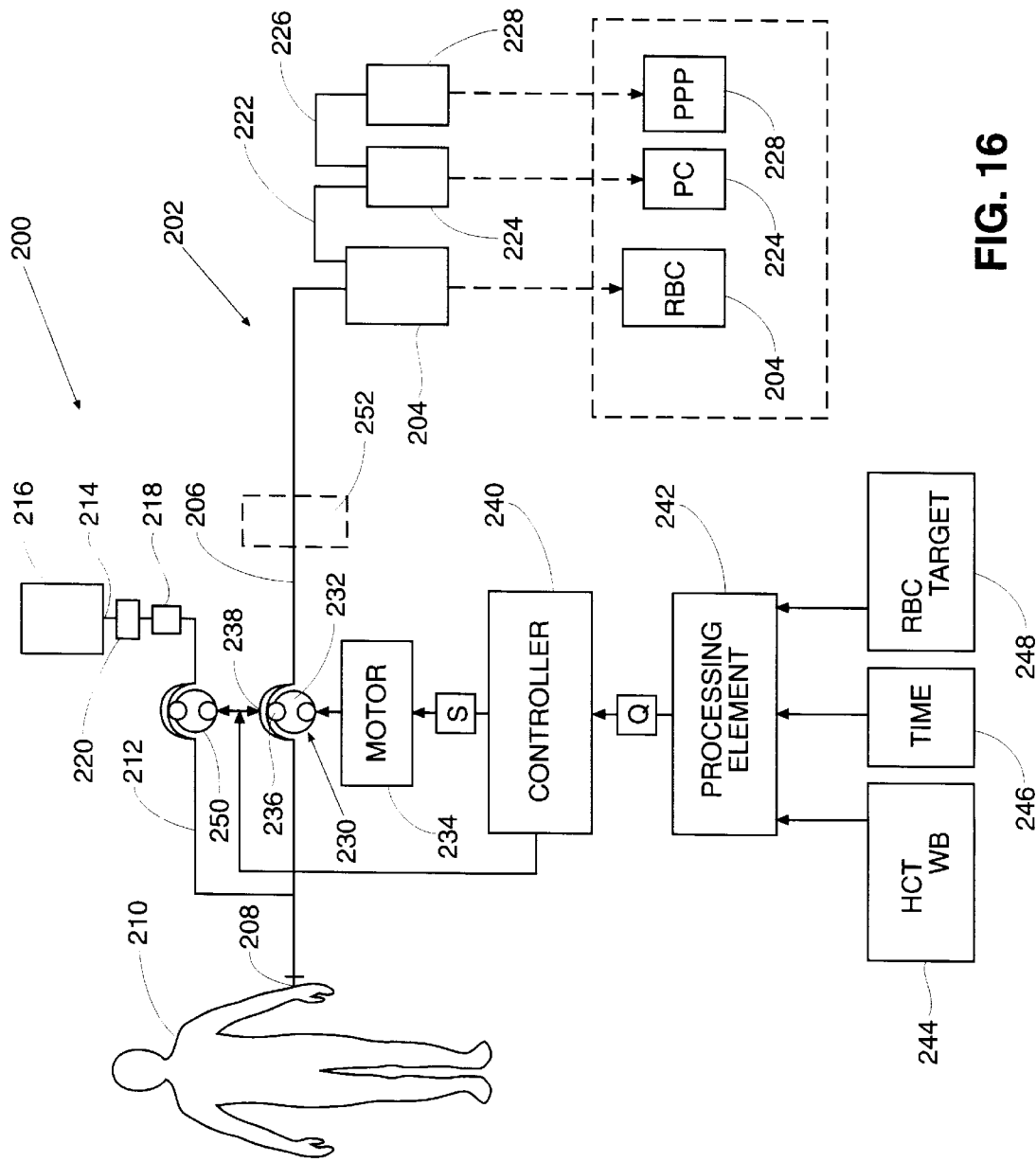
FIG. 16 is a schematic view of a system which, in use, obtains a uniform targeted volume of concentrated red blood cells in diverse donor populations.

FIG. 16 shows another blood processing system 200 which embodies features of the invention.

According to the invention, the system 200 serves to collect a specified uniform volume of concentrated red blood cells from healthy blood donors, despite variations in hematocrit from donor to donor.

The system 200 includes a blood processing set 202, which constitutes a single use, disposable item. The set 202 includes a whole blood collection bag 204 integrally connected to an array of flexible medical grade plastic tubing.

A first tube 206 is integrally connected to the collection bag 204 and carries a phlebotomy needle 208 at its far end. In use, the first tube 206 conveys whole blood from a phlebotomized donor 210 into the collection bag 204.

A second tube 212 communicates with the first tube 206 near the phlebotomy needle 208. The second tube 212 carries a conventional spike coupler 214 for connection to a container 216 holding a conventional anticoagulant, like ACD. The second tube 212 can also include an in line drip chamber 218 and a sterility filter 220. Alternatively, the second tube 212 can be integrally connected to the container 216 during manufacture, or be connected to the container 216 during use with a conventional sterile connection device. In use, the second tube 212 conveys anticoagulant for mixing with whole blood in the first tube 206.

A third tube 222 is integrally connected to the collection bag 204. The third tube 222 is also integrally connected to a first transfer bag 224. A fourth tube 226 integrally connects the first transfer bag 224 to a second transfer bag 228.

The collection bag 204, transfer bags 224 and 228, as associated tubes constitutes a conventional multiple blood bag system. In use, once whole blood is collected in the collection bag 204, the first tube 206 is severed and sealed, using a conventional manual tube sealer.

The collection bag 204 (now containing the donor's whole blood) and transfer bags 224 and 228 are placed as an interconnected unit in a blood centrifuge. Whole blood is separated by centrifugal force within the collection container into concentrated red blood cells and platelet-rich plasma. A majority of leukocytes present in the donor's whole blood will reside principally with either the concentrated red blood cells or the platelet-rich plasma, depending upon strength of the centrifugal field imposed during separation. Generally speaking, the higher the centrifugal force, the greater the number of leukocytes residing with the red blood cells.

Using a conventional V-shape press or the like, the platelet-rich plasma is manually expressed from the collection bag 204 into the first transfer bag 224. The third tube 222 is severed and sealed in conventional sterile fashion, separating the transfer bags 224 and 228 as an interconnected unit from the collection bag 204.

This leaves the concentrated red blood cells (designated RBC) in the collection bag 204, in which they are stored in conventional fashion for later transfusion.

The platelet-rich plasma is separated by centrifugal force in the first transfer bag 224 into concentrated platelets (designated PC in FIG. 16) and platelet-poor plasma (designated PPP in FIG. 16). The platelet poor plasma is manually expressed through the fourth tube 226 into the second transfer bag 228, leaving the concentrated platelets in the first transfer bag 224.

The fourth tube 226 is severed and sealed in conventional sterile fashion, so that the concentrated platelets and platelet-poor plasma can be individually stored for later transfusion in, respectively, the first and second transfer bags 224 and 228.

Conventional whole blood collection protocols typically collect about 450 ml±45 ml in the collection bag 204. The volume of concentrated red blood cells separated during centrifugation will, of course, vary, depending upon the hematocrit of the individual donor. As previously stated, the hematocrit for a typical healthy donor before centrifugation is about 40% to 45%, although whole blood hematocrits do vary significantly among donors from the 30 percentile range into the 50 percentile range. In the United States, federal regulations prohibit individuals with whole blood hematocrits of 38% and below from donating blood. Thus, the volume of concentrated red blood cells collected during a typical manual procedure can vary significantly from 175.5 ml (for donor having a minimum hematocrit of 39%) to 225 ml (for donor having a hematocrit of 50%), and more.

The system 200 shown in FIG. 16 includes a variable speed whole blood inlet pump 230. The pump 230 includes a peristaltic pump rotor assembly 232 driven by a motor 234. Various types of motors 234 can be used, e.g., a brushless D.C. motor. The rotor assembly 232 includes a pair of diametrically spaced rollers 236. In use, the rollers 236 engage the first tube 206 against an associated pump race 238. When rotated, the rollers 236 to press against and urge whole blood from the donor 210 through the first tube 206 into the collection bag 204 at a given flow rate Q. This peristaltic pumping action is well known.

A pump motor controller 240 controls power to the pump motor 240. The controller 240 sends command signals to maintain a desired pump speed S (expressed in revolutions per minute) based upon a desired fluid flow rate Q (in ml/min) through the first tube 206.

The relationship between the desired fluid flow rate Q and the command pump speed S is expressed as follows:

$$S = Q \times k$$

where:
k (in rev/ml) is a pump calibration coefficient, which expresses the fluid volume that is displaced by one revolution of the pump rotor assembly 232. As is known, the pump calibration coefficient k is a function, in part, of the dimension and physical characteristics of the first tube 206 and phlebotomy needle 208, as well as the dimension and physical characteristics of the pump rotor assembly 232. These dimensional and physical relationships can be readily determined empirically.

The pump motor controller 240 includes a processing element 242 having three inputs 244, 246, and 248. The first input 244 receives from the operator a value $HCT_{WB}$, which represents the hematocrit of the individual donor 210. The value $HCT_{WB}$ is determined by analyzing a sample of the donor's blood prior to collection, using conventional techniques.

The second input 246 receives from the operator a value TIME, which represents the time during which whole blood will be collected from the donor 210. A typical value for TIME can be about 7 minutes.

The third input 248 receives from the operator a value $RBC_{TARGET}$, which represents the volume of concentrated red blood cells targeted to be collected from the donor. A typical value for $RBC_{TARGET}$ can be 189 ml, which represents a mean volume of concentrated red blood cells, based upon the assumption that a mean whole blood volume of 450 ml is collected from an average healthy donor having a mean hematocrit value of 42%.

The processing element 242 derives the desired pump flow rate Q based upon the three inputs, as follows:

$$Q = \frac{RBC_{TARGET}}{HCT_{RBC} \times TIME}$$

where:

Q is expressed in ml/min;

$RBC_{TARGET}$ is expressed in ml;

$HCT_{RBC}$ is expressed as a decimal percentage (e.g., 42% is 0.42); and

TIME is expressed in minutes.

The processing element 242 provides as an output the derived rate quantity Q to the pump motor controller 234. Based upon the quantity Q, the motor controller 234 sends command signals to maintain a desired pump speed S, in the manner described above.

In the illustrated embodiment, a second peristaltic pump 250 is coupled in line with the second tube 212. The controller 240 also commands a flow rate of anticoagulant through the second tube 212 to achieve a desired anticoagulant-to-whole blood ratio AC, which will vary as the derived value Q varies.

The system 200 is therefore able to obtain from a diverse population of healthy donors, in which whole blood hematocrit values vary significantly, a fixed collection volume of concentrated red blood cells.

For example, given:

$RBC_{TARGET}$=189 ml, and

TIME=7 minutes, whole blood from a donor having $HCT_{WB}$=0.4 (40%) will be pumped into the collection bag 204 at derived value Q=67.5 ml/min, whereas whole blood from a donor having $HCT_{WB}$= 0.5 (50%) will be pumped into the collection bag 204 at lesser derived rate value Q=54 ml/min.

The system 200 eliminates unit to unit variability caused by different donor hematocrits. The system 200 makes it possible to standardize the volume of concentrated red blood cells collected in a diverse population of healthy donors. Use of the system 200 allows physicians to prescribe and deliver consistent, standardized volumes of concentrated red blood cells during transfusion.

As shown in phantom lines in FIG. 16, the population of leukocytes in the collected blood products can be reduced by placing an in line leukocyte reduction filter 252 in the first tube 206 between the pump 230 and the collection bag 204. The filter 252 can be of conventional construction to remove leukocytes from the whole blood as it is being collected at the rate Q derived for the individual donor to achieve a desired volume of concentrated red blood cells.

Other components of the system 200 can be varied, with or without variation of Q, to achieve the collection of more uniform volumes of concentrated red blood cells from donors having different hematocrits. For example, the set 202 can include a smaller phlebotomy needle 208 (e.g., 18 gauge, instead of 16 gauge) when the blood donor's hematocrit is higher than the 42% mean, thereby dictating a slower rate of collection to achieve the targeted volume of concentrated red blood cells.

Various features of the invention are set forth in the claims that follow.

We claim:

1. A blood separation system comprising
   an inlet line to draw whole blood from a blood donor selected from a population of blood donors, the whole blood of the selected blood donor having a known hematocrit value that varies within the population of blood donors according to morphology of the selected blood donor, the inlet line including a collection container to collect a volume of the whole blood for processing, after severing the inlet line, in an off-line centrifuge into a plasma constituent and a volume of concentrated red blood cells,
   a first input for receiving the known hematocrit value of the selected blood donor,
   a second input for receiving a targeted collection time value,
   a third input for receiving a targeted volume value for the concentrated red blood cells,
   an inlet pump in the inlet line to convey a volume of whole blood from the donor at a commanded flow rate into the collection container, and
   control means coupled to the input for setting the commanded flow rate to vary the volume of whole blood conveyed over time as a function of the known hematocrit value of the selected donor, the targeted collection time value, and the targeted volume value for the concentrated red blood cells to obtain, after off-line centrifugal processing, a targeted volume of concentrated red blood cells for any donor in the population of blood donors, despite variances in known hematocrit values among the donors.

2. A system according to claim 1 further including at least one transfer container coupled to the blood collection container to receive the plasma constituent after centrifugal processing.

3. A system according to claim 1 wherein the inlet line includes a device to separate leukocytes from the volume of whole blood.

4. A system according to claim 1 wherein the inlet line includes a source of anticoagulant for mixing with the volume of whole blood.

5. A system according to claim 4 and further including a pump for mixing anticoagulant with the whole blood at a set anticoagulant-to-whole blood ratio.

6. A blood separation method comprising the steps of
   drawing whole blood from a blood donor through an inlet line into a blood collection container, the blood donor being selected from a population of blood donors, the whole blood of the selected blood donor having a known hematocrit value that varies within the population of blood donors according to morphology of the selected blood donor,
   recording the known hematocrit value of the selected blood donor,
   recording a targeted collection time,
   recording a targeted volume of concentrated red blood cells,
   operating a pump in the inlet line to convey a volume of whole blood from the donor into the blood collection container at a commanded flow rate
   setting the commanded flow rate to vary the volume of whole blood conveyed into the blood collection container over time as a function of the known hematocrit value of the selected donor, the targeted collection time, and the targeted volume of concentrated red blood cells,
   severing the inlet line to terminate collection of whole blood in the blood collection container, and
   centrifugally separating the volume of whole blood in the collection container to obtain a plasma constituent and the targeted volume of concentrated red blood cells for any donor in the population of blood donors, despite variances in known hematocrit values among the donors.

7. A method according to claim 6
wherein the pump operating step conveys the volume of whole blood through a device to separate leukocytes from the volume of whole blood.

8. A method according to claim 6
wherein the blood drawing step includes mixing anticoagulant with the volume of whole blood.

9. A method according to claim 6 further including the step of conveying the plasma constituent from the blood collection container into a transfer container.

* * * * *

UNITED STATES PATENT AND TRADEMARK OFFICE
CERTIFICATE OF CORRECTION

PATENT NO. : 6,251,284 B1
DATED : June 26, 2001
INVENTOR(S) : Bischof et al.

It is certified that error appears in the above-identified patent and that said Letters Patent is hereby corrected as shown below:

<u>Title page,</u>
Item [75], Inventors, Jose C. Deniega, Lake Forest; Daniel H. Duff, Irvine, both of CA (US) are deleted as inventors.

Signed and Sealed this

Tenth Day of September, 2002

Attest:

JAMES E. ROGAN
Attesting Officer  *Director of the United States Patent and Trademark Office*